(12) United States Patent
Kitamura et al.

(10) Patent No.: US 10,898,112 B2
(45) Date of Patent: Jan. 26, 2021

(54) GAIT POSTURE METER AND PROGRAM

(71) Applicant: OMRON HEALTHCARE CO., LTD., Muko (JP)

(72) Inventors: Yumi Kitamura, Kyoto (JP); Naoki Takeishi, Kyoto (JP); Yuji Asada, Kyoto (JP); Fumihiko Nakamura, Kyoto (JP); Kazuya Uemura, Kyoto (JP); Tamaki Ito, Kyoto (JP)

(73) Assignee: OMRON HEALTHCARE CO., LTD., Kyoto (JP)

( * ) Notice: Subject to any disclaimer, the term of this patent is extended or adjusted under 35 U.S.C. 154(b) by 624 days.

(21) Appl. No.: 14/918,985

(22) Filed: Oct. 21, 2015

(65) Prior Publication Data

US 2016/0038060 A1 Feb. 11, 2016

Related U.S. Application Data

(63) Continuation of application No. PCT/JP2014/058914, filed on Mar. 27, 2014.

(30) Foreign Application Priority Data

May 10, 2013 (JP) ................. 2013-100622

(51) Int. Cl.
*A61B 5/11* (2006.01)
*A61B 5/00* (2006.01)

(52) U.S. Cl.
CPC ............ *A61B 5/112* (2013.01); *A61B 5/1116* (2013.01); *A61B 5/6823* (2013.01); *A61B 2562/0219* (2013.01)

(58) Field of Classification Search
None
See application file for complete search history.

(56) References Cited

U.S. PATENT DOCUMENTS 8,573,982 B1 * 11/2013 Chuang .............. G09B 19/0038
434/255
2009/0240461 A1 * 9/2009 Makino ................ G01C 22/006
702/141

(Continued)

FOREIGN PATENT DOCUMENTS

JP 2011-78534 A 4/2011
JP 2011-251013 A 12/2011

(Continued)

OTHER PUBLICATIONS

Official Communication issued in International Patent Application No. PCT/JP2014/058914, dated May 13, 2014.

(Continued)

*Primary Examiner* — Patrick Fernandes
*Assistant Examiner* — Benjamin S Melhus
(74) *Attorney, Agent, or Firm* — Keating and Bennett, LLP

(57) ABSTRACT

A gait posture meter evaluates a gait posture of a measurement subject, and includes an accelerometer affixed to a centerline of a measurement subject's waist area, an evaluation unit that repeatedly finds an evaluation amount quantitatively expressing a gait posture of the measurement subject based on an output of the accelerometer in each of predetermined unit periods within a predetermined continuous walking period of no greater than ten minutes, and a display processing unit that displays the repeatedly-found evaluation amounts in time series in the display screen.

9 Claims, 19 Drawing Sheets

(56) References Cited

U.S. PATENT DOCUMENTS

| | | | |
|---|---|---|---|
| 2010/0227302 A1* | 9/2010 | McGilvery | G09B 19/0038 |
| | | | 434/236 |
| 2012/0101771 A1 | 4/2012 | Kentaro | |
| 2012/0116550 A1* | 5/2012 | Hoffman | A63B 24/0084 |
| | | | 700/91 |
| 2013/0002264 A1 | 1/2013 | Garber | |
| 2013/0041617 A1* | 2/2013 | Pease | A61B 5/02438 |
| | | | 702/139 |
| 2013/0090574 A1 | 4/2013 | Kuribayashi et al. | |
| 2013/0158686 A1* | 6/2013 | Zhang | A61B 5/1123 |
| | | | 700/91 |
| 2015/0272480 A1* | 10/2015 | Senta | A61B 5/725 |
| | | | 600/595 |

FOREIGN PATENT DOCUMENTS

| | | |
|---|---|---|
| JP | 2013-13734 A | 1/2013 |
| WO | 2012/036135 A1 | 3/2012 |

OTHER PUBLICATIONS

Ozaki et al., "Basic Study on the Effect of Footwear Type on Gait", J. Jpn. Soc. Nurs. Health Care, vol. 13, No. 2, 2011, pp. 56-65.

* cited by examiner (A)

(B)

GAIT POSTURE METER AND PROGRAM

BACKGROUND OF THE INVENTION

1. Field of the Invention

This invention relates to gait posture meters, and particularly relates to a gait posture meter that quantitatively evaluates whether or not a person's gait posture is a correct posture.

This invention also relates to a program for causing a computer to execute a method that quantitatively evaluates whether or not a person's gait posture is a correct posture.

2. Description of the Related Art

A gait posture meter that evaluates the left-right balance of a stride, the left-right balance of a center of gravity, and so on using an output from an accelerometer affixed to a measurement subject and displays an evaluation result as a bubble chart of positions or sizes based on the evaluation has been proposed as this type of device, as disclosed in JP 2011-078534A, for example (see JP 2011-078534A 1, FIGS. 10, 14, 18, and so on).

There is also a mobile electronic device that, based on outputs from a six-axis sensor (a three-axis accelerometer and a three-axis angular velocity sensor) affixed to a measurement subject, finds a movement amount and a rotation amount for each axis, and evaluates a gait posture based thereon, as disclosed in JP 2011-251013A, for example. The mobile electronic device according to JP 2011-251013A displays a result of the evaluation as points on a scale up to 100 (see JP 2011-251013A, FIG. 25(G)).

SUMMARY OF THE INVENTION

However, the conventional devices have not focused on periods in which a person walks continuously in his/her normal everyday life, such as ten minutes at the most, for example, continually evaluated the gait posture throughout that period, and notified a user of transitions (positive and negative changes over time) in the gait posture within that period. Accordingly, it has been difficult for a user to know information such as whether or not s/he is continually walking correctly in his/her everyday periods of walking, at what timing his/her gait posture has worsened, and so on.

In light of the foregoing, an aspect of the present invention provides a gait posture meter capable of presenting to a user, in an easily-understandable manner, a positive and negative transition over time in the user's gait posture when walking continuously in his/her everyday life.

In addition, another aspect of the present invention provides a program that causes a computer to execute a method capable of presenting to a user, in an easily-understandable manner, a positive and negative transition over time in the user's gait posture when walking continuously in his/her everyday life.

To solve the aforementioned problems, a gait posture meter according to an aspect of the present invention is a gait posture meter that evaluates a gait posture of a measurement subject, the meter including an accelerometer affixed to a centerline of a measurement subject's waist area, an evaluation unit that repeatedly finds an evaluation amount quantitatively expressing a gait posture of the measurement subject based on an output of the accelerometer in each of predetermined unit periods within a predetermined continuous walking period of no greater than ten minutes, and a display processing unit that displays the repeatedly-found evaluation amounts in time series in the display screen; in each unit period, the evaluation unit obtains the output of the accelerometer only in a pre-set logging period that is shorter than the unit period and finds the evaluation amount for that unit period based on the obtained output.

With the gait posture meter according to this aspect of the present invention, the accelerometer is affixed to the centerline of the measurement subject's waist area. The evaluation unit repeatedly finds an evaluation amount quantitatively expressing a gait posture of the measurement subject based on an output of the accelerometer in each of predetermined unit periods within a predetermined continuous walking period of no greater than ten minutes, and the display processing unit displays the repeatedly-found evaluation amounts in time series in the display screen. Accordingly, this gait posture meter continually evaluates the gait posture throughout a period in which a person walks continuously in his/her normal everyday life, such as ten minutes at the most, for example, and notifies a user of transitions (positive and negative changes over time) in the gait posture within that period. As such, the user can know positive and negative transitions in his/her gait posture over an everyday continuous walking period, and can easily know periods (unit periods) in which s/he walked well in everyday continuous walking and periods (unit periods) in which such was not the case. Furthermore, with this gait posture meter, the output of the accelerometer is obtained only in a logging period that is shorter than the unit period. In other words, this gait posture meter obtains (logs) the output of the accelerometer intermittently, rather than obtaining the output throughout the entire unit period. Accordingly, the amount of power consumed by the gait posture meter can be suppressed.

In a gait posture meter according to an embodiment, the display processing unit displays the repeatedly-found evaluation amounts in the display screen as a bar graph or a polygonal line graph.

With the gait posture meter according to this embodiment, the user can be notified of positive and negative transitions in his/her gait posture throughout an everyday continuous walking period visually, in an easy-to-understand manner.

In a gait posture meter according to an embodiment, a reference value regarding a dominance of the evaluation amounts is set in advance, and in the display of the bar graph or the polygonal line graph, the display processing unit displays a part of the bar graph or the polygonal line graph corresponding to a value greater than or equal to the reference value in an emphasized manner.

With the gait posture meter according to this embodiment, the user can more intuitively know periods (unit periods) in his/her everyday walking in which s/he walked well.

A gait posture meter according to an embodiment further includes a rank determination unit that sets a rank of dominances among the repeatedly-found evaluation amounts, and of the repeatedly-found evaluation amounts, the display processing unit displays evaluation amounts in the highest predetermined number of rankings in a different manner than the manner in which other evaluation amounts are displayed.

With the gait posture meter according to this embodiment, the user can know periods (unit periods) in his/her everyday walking in which s/he walked well at a glance.

A gait posture meter according to an embodiment further includes an error determination unit that determines whether or not to find the evaluation amount for each unit period based on the output of the accelerometer, and in the case where the error determination unit has determined that the evaluation amount cannot be found for a given unit period, the display processing unit carried out an error display for that unit period instead of displaying the evaluation amount.

With the gait posture meter according to this embodiment, evaluation amounts are not displayed for periods (unit periods) in which the gait posture meter could not correctly evaluate the gait posture of the measurement subject. Accordingly, the user will not see evaluations made when the gait posture meter could not correctly evaluate the gait posture of the measurement subject, and the user can be prevented from having a mistaken understanding of his/her gait posture.

A gait posture meter according to an embodiment further includes a score calculation unit that finds a score by totaling or averaging the evaluation amounts corresponding to the highest rankings and a score display processing unit that displays the score found by the score calculation unit in the display screen.

With the gait posture meter according to this embodiment, a score based only on periods (unit periods) of good walking in the walking period can be displayed. Accordingly, the user can be notified of his/her progress toward improving his/her gait posture in periods (walking periods), during everyday continuous walking, in which it is particularly easy to improve his/her gait posture, more than in the case where a total or an average of the evaluation amounts for all periods (unit periods) is derived as the score. Having viewed the score derived in this manner, the user can quickly know his/her progress toward improving his/her gait posture. This can further increase the user's desire to improve his/her gait posture, which in turn makes it possible to encourage the user to improve his/her gait posture.

A gait posture meter according to an embodiment further includes a storage unit that stores the repeatedly-found evaluation amounts, and the storage unit stores data regarding walking conditions of the measurement subject in association with the repeatedly-found evaluation amounts.

With the gait posture meter according to this embodiment, data regarding the measurement subject's walking conditions that may affect the result of evaluating the gait posture can be stored in association with the evaluation amounts, and thus information useful in analyzing the gait posture can be stored.

A gait posture meter according to an embodiment further includes a condition input unit that accepts information of footwear used when the measurement subject walks; using the information accepted by the condition input unit, the storage unit stores data regarding a type of footwear worn when the measurement subject walks as the data regarding the walking conditions, and the display processing unit displays information indicating the type of the footwear in the display screen.

With the gait posture meter according to this embodiment, information regarding the measurement subject's footwear that may affect the measurement subject's gait posture can be stored. Accordingly, information required for an analysis that takes into consideration the influence of footwear when analyzing the gait posture can be stored along with the evaluation amount. Note that the type of footwear may include slippers, sandals, sneakers, high-heels, and the like, as well as bare feet, and furthermore is not limited thereto.

A program according to another aspect of the present invention is a program for causing a computer to execute a method for evaluating a gait posture of a measurement subject, the method including a step of obtaining an output of an accelerometer that is affixed to a centerline of the measurement subject's waist area, a step of repeatedly finding an evaluation amount quantitatively expressing a gait posture of the measurement subject based on an output of the accelerometer in each of predetermined unit periods within a predetermined continuous walking period of no greater than ten minutes, and a step of displaying the repeatedly-found evaluation amounts in time series in the display screen; in each unit period, the step of obtaining obtains the output of the accelerometer only in a pre-set logging period that is shorter than the unit period, and the step of repeatedly finding an evaluation amount finds the evaluation amount for that unit period based on the output obtained in the step of obtaining.

By executing this program, the computer first obtains the output of the accelerometer that is affixed to the centerline of the measurement subject's waist area. The computer repeatedly finds an evaluation amount quantitatively expressing a gait posture of the measurement subject based on an output of the accelerometer in each of predetermined unit periods within a predetermined continuous walking period of no greater than ten minutes, and displays the repeatedly-found evaluation amounts in time series in the display screen. Accordingly, the computer continually evaluates the gait posture throughout a period in which a person walks continuously in his/her normal everyday life, such as ten minutes at the most, for example, and notifies a user of transitions (positive and negative changes over time) in the gait posture within that period. As such, the user can know positive and negative transitions in his/her gait posture over an everyday continuous walking period, and can easily know periods (unit periods) in which s/he walked well in everyday walking and periods (unit periods) in which such was not the case. Furthermore, with this program, the output of the accelerometer is obtained only in a logging period that is shorter than the unit period. In other words, this program obtains (logs) the output of the accelerometer intermittently, rather than obtaining the output throughout the entire unit period. Accordingly, the amount of power consumed by the computer can be suppressed.

A gait posture meter according to yet another aspect of the present invention is a gait posture meter that evaluates a gait posture of a measurement subject, the meter including an accelerometer affixed to a centerline of a measurement subject's waist area, an evaluation unit that repeatedly finds an evaluation amount quantitatively expressing a gait posture of the measurement subject based on an output of the accelerometer in each of predetermined unit periods within a predetermined continuous walking period, a storage unit that stores the repeatedly-found evaluation amounts, and a condition input unit that accepts information of footwear used when the measurement subject walks; using the information accepted by the condition input unit, the storage unit stores data regarding a type of footwear worn when the measurement subject walks in association with the repeatedly-found evaluation amounts as data regarding walking conditions.

In the gait posture meter according to this other aspect of the present invention, the accelerometer is affixed to the centerline of the measurement subject's waist area. The evaluation unit repeatedly finds an evaluation amount quantitatively expressing a gait posture of the measurement subject based on an output of the accelerometer in each of predetermined unit periods within a predetermined continuous walking period, and information of the footwear used when the measurement subject walks is obtained by the condition input unit. Then, using the information accepted by the condition input unit, data regarding a type of footwear worn by the measurement subject when walking is stored in the storage unit as data regarding walking conditions, in association with the repeatedly-found evaluation amounts. Accordingly, evaluation amounts regarding the gait posture in everyday walking can be accumulated easily in association with the type of footwear used in that walking, which makes it possible to easily accumulate data useful in analyzing the gait posture in detail.

As is clear from the foregoing, with the gait posture meter according to an aspect of this invention, a user can easily know transitions (positive and negative changes over time) in the gait posture within a period in which the user walks continuously in his/her normal everyday life, such as ten minutes at the most, for example. Accordingly, the user can know information such as whether or not s/he is continually walking correctly in his/her everyday periods of walking, at what timing his/her gait posture has worsened, and so on.

Furthermore, by causing a computer to execute the program according to an aspect of this invention, a user can easily know transitions (positive and negative changes over time) in the gait posture within a period in which the user walks continuously in his/her normal everyday life, such as ten minutes at the most, for example. Accordingly, the user can know information such as whether or not s/he is continually walking correctly in his/her everyday periods of walking, at what timing his/her gait posture has worsened, and so on.

The above and other elements, features, steps, characteristics and advantages of the present invention will become more apparent from the following detailed description of the preferred embodiments with reference to the attached drawings.

BRIEF DESCRIPTION OF THE DRAWINGS

FIG. 8A is a schematic diagram illustrating, from the side, a person whose center of gravity position during walking is in a forward-shifted position. FIG. 8B is a schematic diagram illustrating, from the side, a person whose center of gravity position during walking is near a center position. FIG. 8C is a schematic diagram illustrating, from the side, a person whose center of gravity position during walking is in a rearward-shifted position. FIG. 8D is a typical example of an up-down acceleration time change waveform of a person whose center of gravity position is in a forward-shifted position (FIG. 8A). FIG. 8E is a typical example of an up-down acceleration time change waveform of a person whose center of gravity position is near a center position (FIG. 8B). FIG. 8F is a typical example of an up-down acceleration time change waveform of a person whose center of gravity position is in a rearward-shifted position (FIG. 8C).

DETAILED DESCRIPTION OF THE PREFERRED EMBODIMENTS

Hereinafter, an embodiment of the invention will be described in detail with reference to the drawings.

Figure 1:
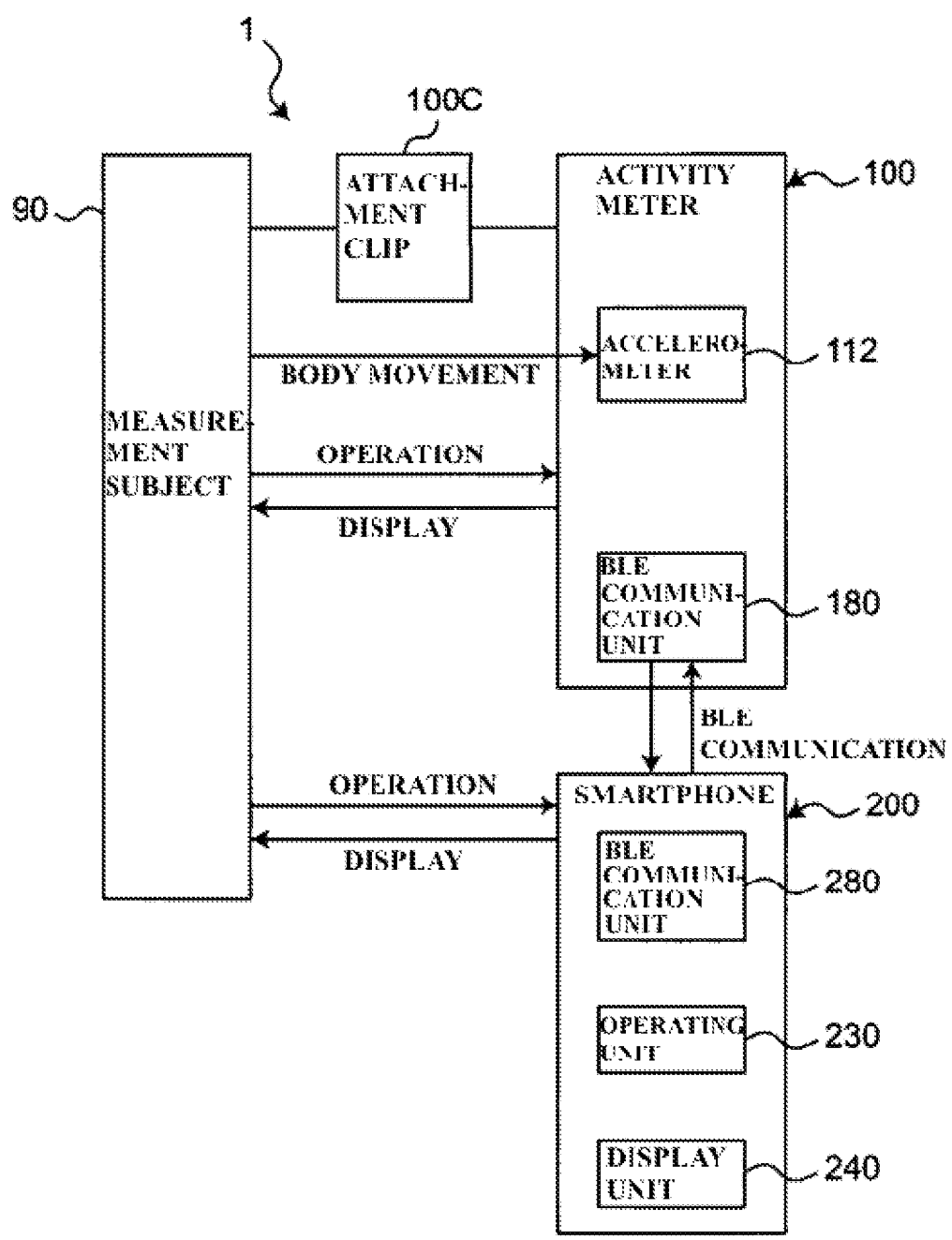
FIG. 1 is a diagram illustrating a system configuration of a gait posture meter according to an embodiment of this invention.

FIG. 1 illustrates a system configuration of a gait posture meter (generally indicated by reference numeral 1) according to an embodiment of this invention. This gait posture meter 1 includes an activity meter 100 and a smartphone 200. In this example, the activity meter 100 and the smartphone 200 are capable of communicating with each other through BLE (Bluetooth Low Energy, a low-power-consumption Bluetooth defined in Bluetooth Core Specification Ver. 4.0) communication.

Figure 2:
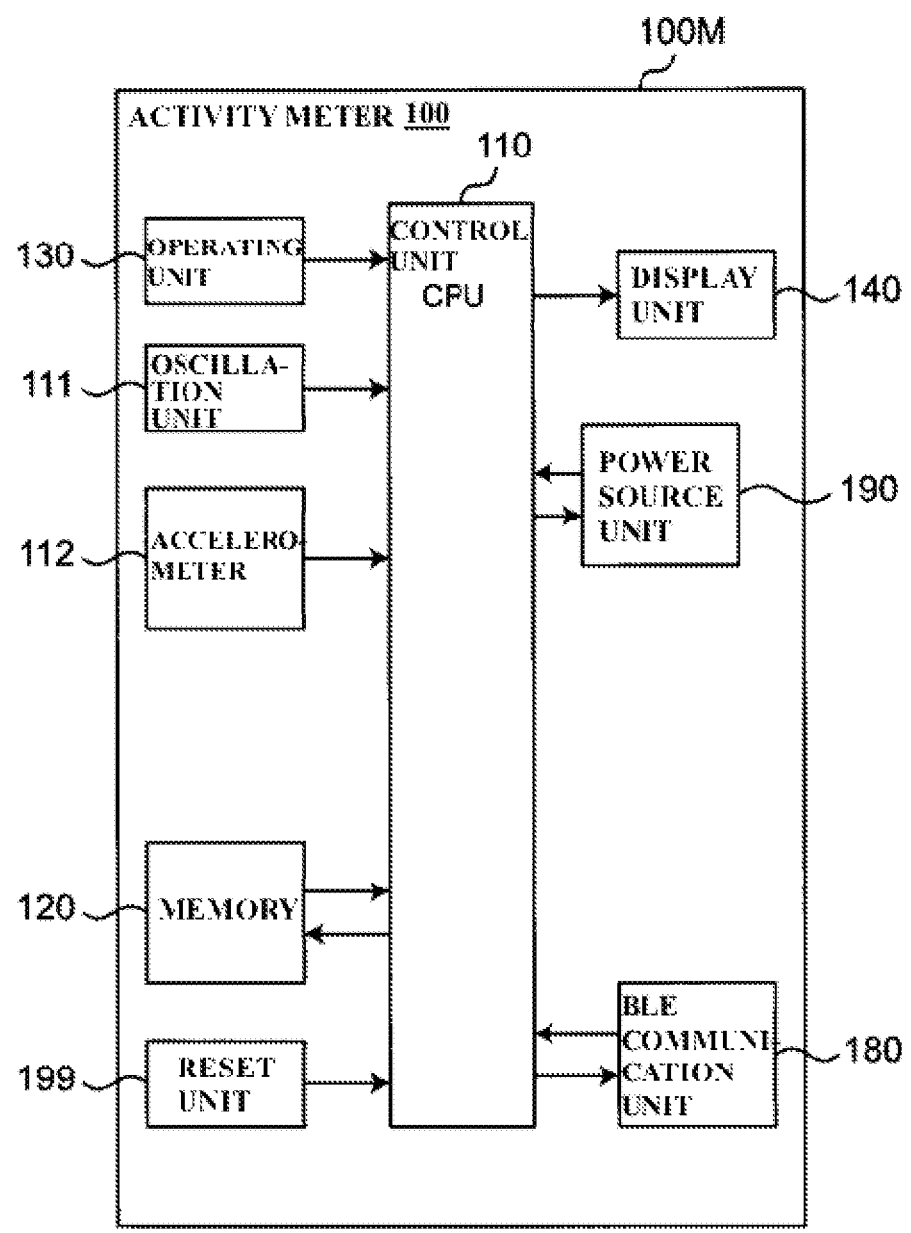
FIG. 2 is a diagram illustrating a block configuration of an activity meter that forms part of the system of the stated gait posture meter.

As illustrated in FIG. 2, the activity meter 100 includes a casing 100M, and a control unit 110, an oscillation unit 111, an accelerometer 112, a memory 120, an operating unit 130, a display unit 140, a BLE communication unit 180, a power source unit 190, and a reset unit 199 provided in the casing 100M.

The casing 100M is formed having a size that fits in the palm of a person's hand so that the activity meter 100 can be carried with ease.

The oscillation unit 111 includes a quartz vibrator, and emits a clock signal that serves as a reference for operational timings in the activity meter 100. The oscillation unit 111 may be a module chip that functions as a clock generator.

The accelerometer 112 detects accelerations in each of three axes (three directions) that the casing 100M is subjected to, and outputs those accelerations to the control unit 110. The accelerometer 112 may be a three-axis accelerometer module chip.

The memory 120 includes a ROM (Read Only Memory) and a RAM (Random Access Memory). The ROM stores data of programs for controlling the activity meter 100. The RAM, meanwhile, stores configuration data for configuring various types of functions of the activity meter 100, acceleration measurement results, data of computational results, and so on. The memory 120 may constitute a storage unit, which will be described in detail below.

The control unit 110 includes a CPU (Central Processing Unit) that operates based on the aforementioned clock signal, and controls the respective units of the activity meter 100 (including the memory 120, the display unit 140, and the BLE communication unit 180) based on detection signals from the accelerometer 112, in accordance with a program for controlling the activity meter 100 stored in the memory 120. The control unit 110 includes a signal processing system capable of processing time-series data of at least one of an up-down axis acceleration, a left-right axis acceleration, and a front-rear axis acceleration. The control unit 110 functions as an evaluation unit and an error determination unit, as will be described in detail below.

The operating unit 130 is in this example constituted of button based switches, and accepts operational inputs as appropriate, such as operations for switching the power on and off, operations for switching display details, and so on.

The display unit 140 includes a display screen that is in this example configured of an LCD (liquid-crystal display) or an organic EL (electroluminescence) display, and displays predetermined information in the display screen in accordance with signals received from the control unit 110. The display unit 140 may function as a notification unit, which will be described in detail below. The display unit 140 may be an LED (light-emitting diode) that displays whether the power is on or off, operational states, or the like by turning on, turning off, blinking, or the like.

The power source unit 190 is in this example a button battery, and supplies power to the various elements of the activity meter 100.

The BLE communication unit 180 communicates with the smartphone 200 in real time. For example, the BLE communication unit 180 sends information indicating measurement results and the like to the smartphone 200. The BLE communication unit 180 also receives operating instructions from the smartphone 200. The BLE communication unit 180 may be a module chip having a BLE function.

The reset unit 199 is constituted of a switch, and resets and initializes operations of the control unit 110, content stored by the memory 120, and so on.

Figure 3:
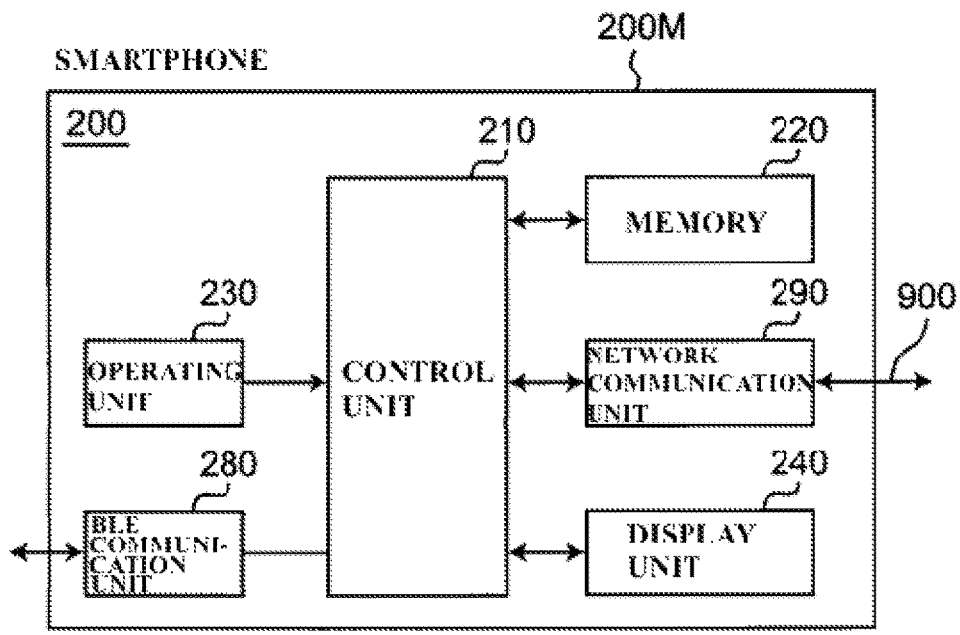
FIG. 3 is a diagram illustrating a block configuration of a smartphone that forms part of the system of the stated gait posture meter.

As illustrated in FIG. 3, the smartphone 200 includes a main body 200M, and a control unit 210, a memory 220, an operating unit 230, a display unit 240, a BLE communication unit 280, and a network communication unit 290 provided in the main body 200M. The smartphone 200 is a commercially-available smartphone in which application software (a computer program) for making instructions to the activity meter 100 has been installed.

The control unit 210 includes a CPU as well as auxiliary circuitry thereof, controls the various units of the smartphone 200, and executes processes in accordance with programs and data stored in the memory 220. In other words, the control unit 210 processes data inputted through the operating unit 230 and the communication units 280 and 290, and stores the processed data in the memory 220, displays the processed data in the display unit 240 (a display screen), outputs the processed data from the communication units 280 and 290, or the like. The control unit 210 can function as a display processing unit, a rank determination unit, a score calculation unit, and a score display processing unit, as will be described in detail below.

The memory 220 includes a RAM used as a work area required by the control unit 210 to execute programs, and a ROM for storing basic programs to be executed by the control unit 210. A semiconductor memory (a memory card, an SSD (Solid State Drive)) or the like may be used as a storage medium in an auxiliary storage unit for complementing a storage region in the memory 220. The memory 220 and the auxiliary storage unit constitute the storage unit, which will be described in detail below.

The operating unit 230 is in this example configured of a touch panel provided on the display unit 240. Note, however, that another hardware-based operating device such as a keyboard may be included as well.

The display unit 240 includes a display screen (constituted by, for example, an LCD or an organic EL display). The display unit 240 displays a predetermined image in the display screen under the control of the control unit 210.

The BLE communication unit 280 communicates with the activity meter 100 in real time. For example, the BLE communication unit 280 sends operating instructions to the activity meter 100. The BLE communication unit 280 also receives information expressing measurement results and the like from the activity meter 100.

The network communication unit 290 sends information from the control unit 210 to another apparatus over a network 900, and receives information sent over the network 900 from another apparatus and passes the information to the control unit 210.

Figure 4:
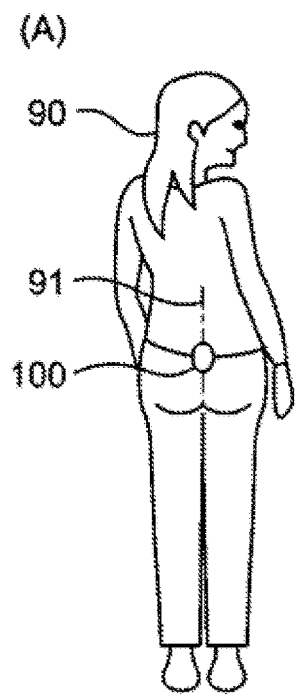
FIG. 4A is a diagram illustrating the activity meter being affixed to a measurement subject.
FIG. 4B is a diagram illustrating an X axis (a front-rear axis), a Y axis (a left-right axis), and a Z axis (an up-down axis).
Figure 4:
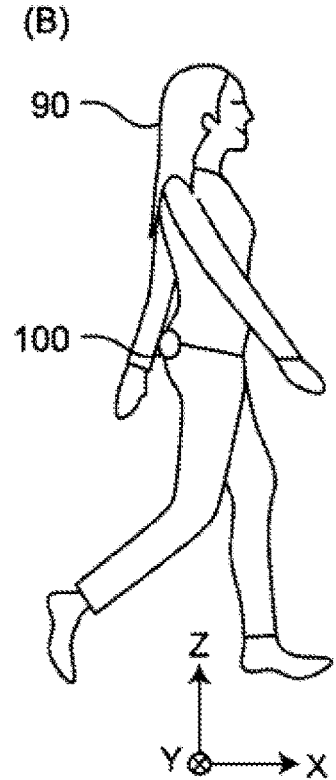

As illustrated in FIG. 4A, in the case where the gait posture meter 1 is used by, for example, a measurement subject 90 serving as a user, the activity meter 100 is affixed at the waist on a rear side of the measurement subject 90, on a centerline 91 thereof, using an attachment clip 100C (indicated in FIG. 1).

In this example, relative to the measurement subject 90, a front-rear direction corresponds to the X axis, a left-right direction corresponds to the Y axis, and an up-down direction corresponds to the Z axis, as illustrated in FIG. 4B. The accelerometer 112 of the activity meter 100 outputs an X axis (front-rear axis) acceleration, a Y axis (left-right axis) acceleration, and a Z axis (up-down axis) acceleration that the casing 100M is subjected to as the measurement subject 90 walks forward.

Figure 12:
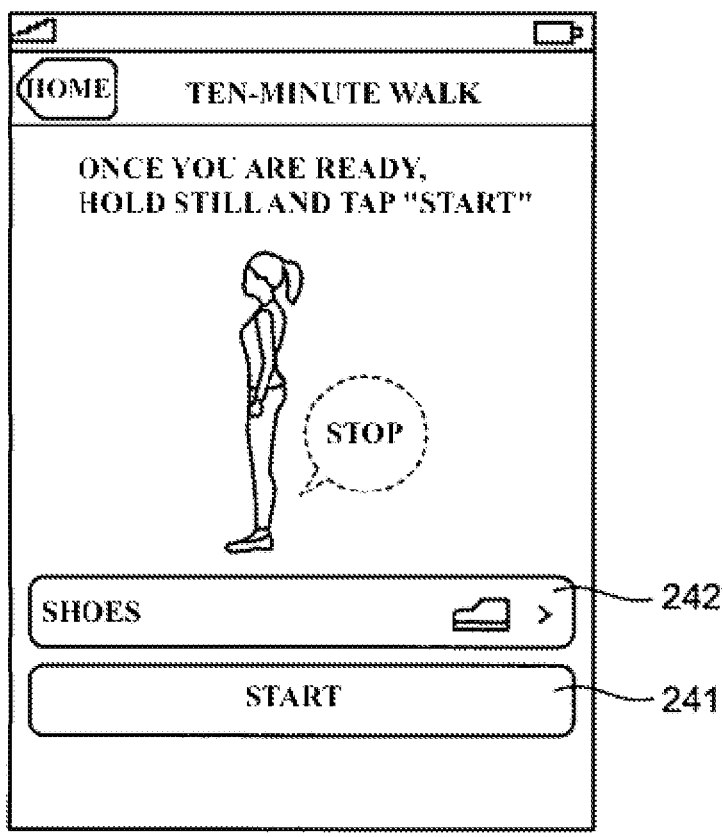
FIG. 12 is a diagram illustrating an example of a display in a display unit (an operating unit) of a smartphone that partially constitutes the gait posture meter.

When a measurement is to be taken using the gait posture meter 1, the measurement subject 90 turns the activity meter 100 and the smartphone 200 on. The measurement subject also launches the application software in the smartphone 200 and instructs the activity meter 100 to start measurement via the operating unit 230 and the BLE communication unit 280 (see FIG. 12). FIG. 12 is an example of a display in the operating unit 230 (the display unit 240) of the smartphone 200. Here, a "start" button 241 is a part that accepts an instruction for starting measurement from the user (the measurement subject 90). In addition, a button 242 is provided in this screen as a button for inputting data regarding the measurement subject's walking conditions. This is a button for inputting information regarding the type of footwear used when walking as data regarding the walking conditions of the user (the measurement subject 90). A menu for selecting the type of footwear is called upon the user tapping the button 242, and the type of footwear used during walking can be inputted by selecting footwear such as bare feet, sandals, high-heels, or the like from the menu. The inputted data is stored in the storage unit (the memory 220 or the like) in association with an evaluation amount of a gait posture and a left-right balance.

In this state, the measurement subject 90 walks normally in his/her everyday life (walks from home to a station, from a station to a workplace, or the like, for example).

Upon doing so, the control unit 110 of the activity meter 100 operates as the evaluation unit, and carries out computations that will be described later. Information expressing the evaluation result is then sent to the smartphone 200 via the BLE communication unit 180. The control unit 210 of the smartphone 200 operates as the display processing unit and displays the evaluation result by carrying out a process that will be described later.

Figure 11:
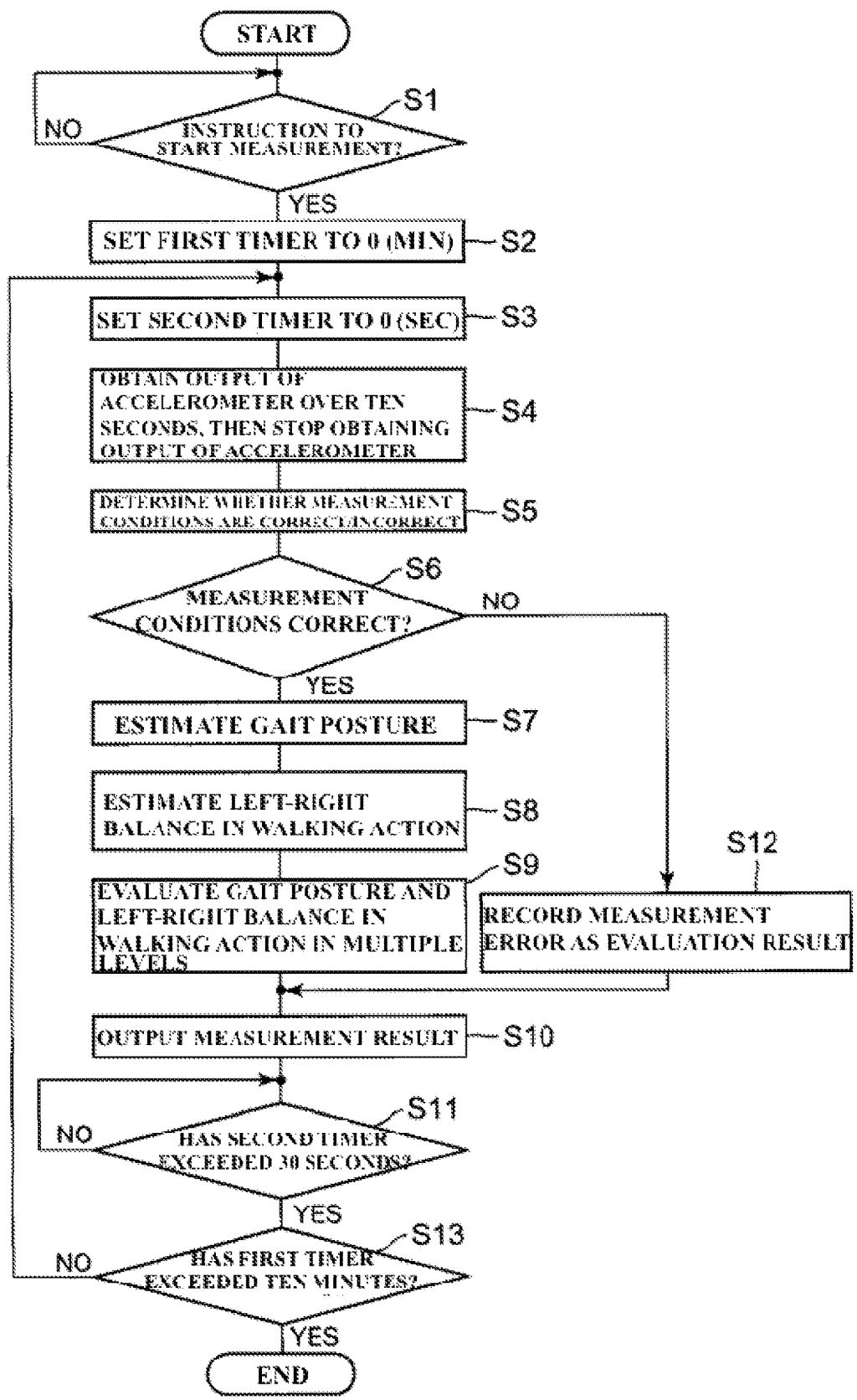
FIG. 11 is a diagram illustrating a flow of operations performed by a control unit of the activity meter that partially constitutes the gait posture meter.

FIG. 11 illustrates a flow of operations performed by the control unit 110 of the activity meter 100 according to this embodiment. When the power is turned on, the control unit 110 of the activity meter 100 stands by for an instruction from the smartphone 200 to start measurement, as indicated in step S1. Upon receiving an instruction to start measurement from the smartphone 200 (YES in step S1), the control unit 110 starts measuring time by a timer that uses an output of the oscillation unit 111, as indicated in step S2 and step S3. In step S2, time measurement is started using a first timer that measures a walking period (ten minutes, for example) that corresponds to everyday continuous walking. In step S3, time measurement is started using a second timer that measures a plurality of gait posture evaluation unit periods (30 seconds, for example) in the walking period. Note that the walking period is not limited to ten minutes. For example, a length of three minutes may be used. Likewise, the unit period is not limited to 30 seconds. For example, a length of one minute may be used.

For the first ten seconds of each unit period (this corresponds to 20 steps' worth of time in the case where the measurement subject's walking cycle is one second, and will be called a "logging period"), the control unit 110 obtains outputs from the accelerometer 112 by operating as the evaluation unit. After obtaining the outputs from the accelerometer 112 for ten seconds, the evaluation unit stops obtaining the outputs of the accelerometer (step S4). The obtainment is stopped here for the purpose of conserving energy.

At the point in time when the process of step S4 has ended, the control unit 110, which serves as the evaluation unit, holds time-series data of a three-axis direction acceleration generated from the output of the accelerometer in the memory 120. Next, by operating as the error determination unit, the control unit 110 determines whether or not the acceleration time-series data in that unit period was measured correctly enough to enable the gait posture to be evaluated correctly, based on the acceleration time-series data in one or more directions (step S5). For example, it is determined whether or not the measurement subject turned a corner, whether or not the measurement subject switched a hand that holds a bag, or the like in that unit period.

In the case where it is determined in step S6 that the acceleration time-series data in that unit period was measured correctly enough to enable the gait posture to be evaluated correctly ("YES" in step S6), the control unit 110 estimates the measurement subject's gait posture (front-rear direction imbalance in the center of gravity, for example) in that unit period by operating as the evaluation unit (step S7). The evaluation unit also estimates a left-right balance (for example, a difference between walking actions when the left leg is the supporting leg and walking actions when the right leg is the supporting leg) in the measurement subject's gait posture in that unit period (step S8). Then, based on the estimations made in step S7 and step S8, the evaluation unit evaluates the measurement subject's gait posture and left-right balance in the unit period in multiple stages (step S9).

On the other hand, in the case where it is determined in step S6 that the acceleration time-series data in that unit period was not measured correctly enough to enable the gait posture to be evaluated correctly ("NO" in step S6), the control unit 110 records data indicating that the measurement subject's gait posture and left-right balance could not be evaluated in that unit period by operating as the evaluation unit (step S12).

In step S10, the evaluation unit outputs a result of the evaluation carried out in step S9 or the data indicating a measurement error recorded in step S12 to the smartphone 200.

The control unit 110 stands by until the time measured by the second timer exceeds 30 seconds (step S11).

When the time measured by the second timer exceeds 30 seconds, the control unit 110 determines whether or not the time measured by the first timer has exceeded ten minutes (step S13). In the case where the time measured by the first timer does not exceed ten minutes ("NO" in step S13), the process moves to step S3. In the case where the time measured by the first timer has exceeded ten minutes ("YES" in step S13), the process ends.

Hereinafter, the processing carried out by the control unit 110 as illustrated in FIG. 11 will be described in detail with reference to FIGS. 5, 6A, 6B, 7A, 7B, 8, 9, and 10.

Figure 5:
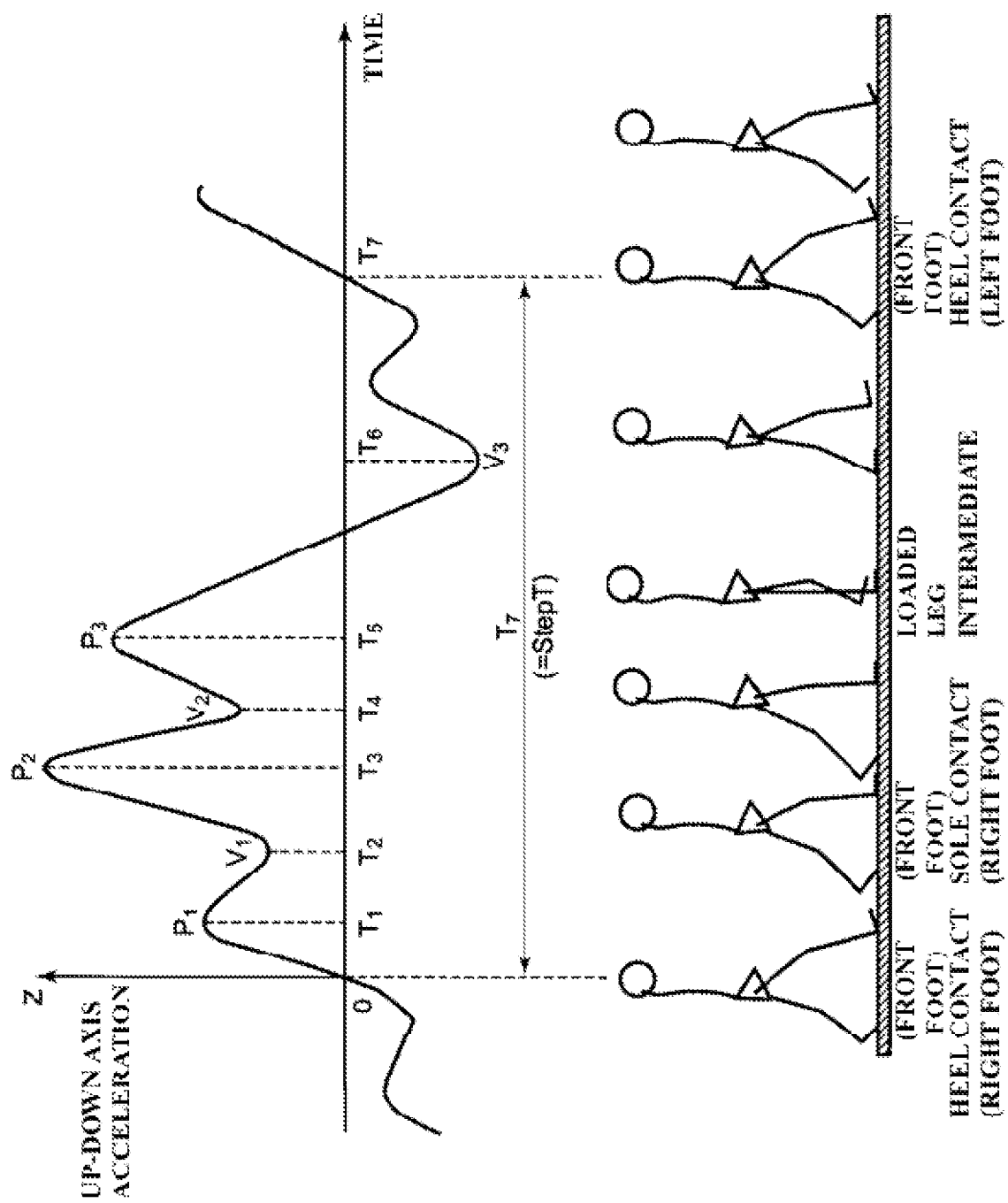
FIG. 5 is a diagram illustrating a relationship between an example (in the time domain) of an up-down axis acceleration measured by an accelerometer affixed to a person's waist while the person is walking, a reference period corresponding to one step's worth of a walking cycle, and one step's worth of gait.

FIG. 5 is a diagram illustrating a relationship between a person's gait and a typical example of a time change waveform of the up-down axis acceleration (a Z axis direction acceleration that takes a vertical upward direction as positive) outputted from the accelerometer 112 of the activity meter 100 affixed to the waist during a reference period (T7 in FIG. 5 (=StepT)) that corresponds to one step's worth of a walking cycle.

The up-down axis acceleration passes through a zero crossing point and switches from negative to positive near a timing at which the heel of the front foot (the right foot, in FIG. 5) that has been put out makes contact with a movement surface (a heel contact timing).

Thereafter, three peaks (maximum points) (P1 (time t=T1), P2 (time t=T3), and P3 (time t=T5)), as well as interposing valleys (minimum points) (V1 (time t=T2) and V2 (time t=T4)) appear in the up-down axis acceleration. In the person's gait, a timing at which the loaded leg (the right leg in FIG. 5) and the lifted leg (the left leg in FIG. 5) essentially match with respect to the travel direction (a loaded leg intermediate timing) corresponds to the vicinity of the timing at which the third peak P3 appears.

When, in the person's gait, the loaded leg intermediate timing is passed, the up-down axis acceleration once again passes through the zero crossing point and switches from positive to negative, passes through a minimum point (V3 (time t=T6)), and ultimately passes through the zero crossing point (time t=T7) again at time t=T7 and switches from negative to positive. The zero crossing point at time t=T7 corresponds to the heel contact timing of the next step (in which the left foot is the front foot, in FIG. 5).

In this manner, a waveform appears in the up-down axis acceleration while a person walks one step, as described with reference to FIG. 5. In the present specification, a period (StepT) spanning from the timing at which the heel of the front foot makes contact with the ground (the heel contact timing) to the next heel contact timing is defined as the reference period. Only when is particularly necessary to make a distinction, reference periods for one step by the left foot and one step by the right foot will be distinguished from each other in the following descriptions by referring to a period spanning from the heel contact timing for the left foot to the heel contact timing for the right foot as a left foot reference period and a period spanning from the heel contact timing for the right foot to the heel contact timing for the left foot as a right foot reference period.

In the timewise change waveform of the up-down axis acceleration that takes the upward direction as positive, a period spanning from the timing at which the zero crossing point where the acceleration value changes from negative to positive appears to the timing at which the next zero crossing point where the change from negative to positive appears corresponds to a single reference period.

Next, the determination, carried out by the control unit 110 operating as the error determination unit, as to whether or not the acceleration time-series data has been measured correctly enough to enable the gait posture to be evaluated correctly will be described with reference to FIGS. 6A, 6B, 7A, and 7B.

Figure 6A:
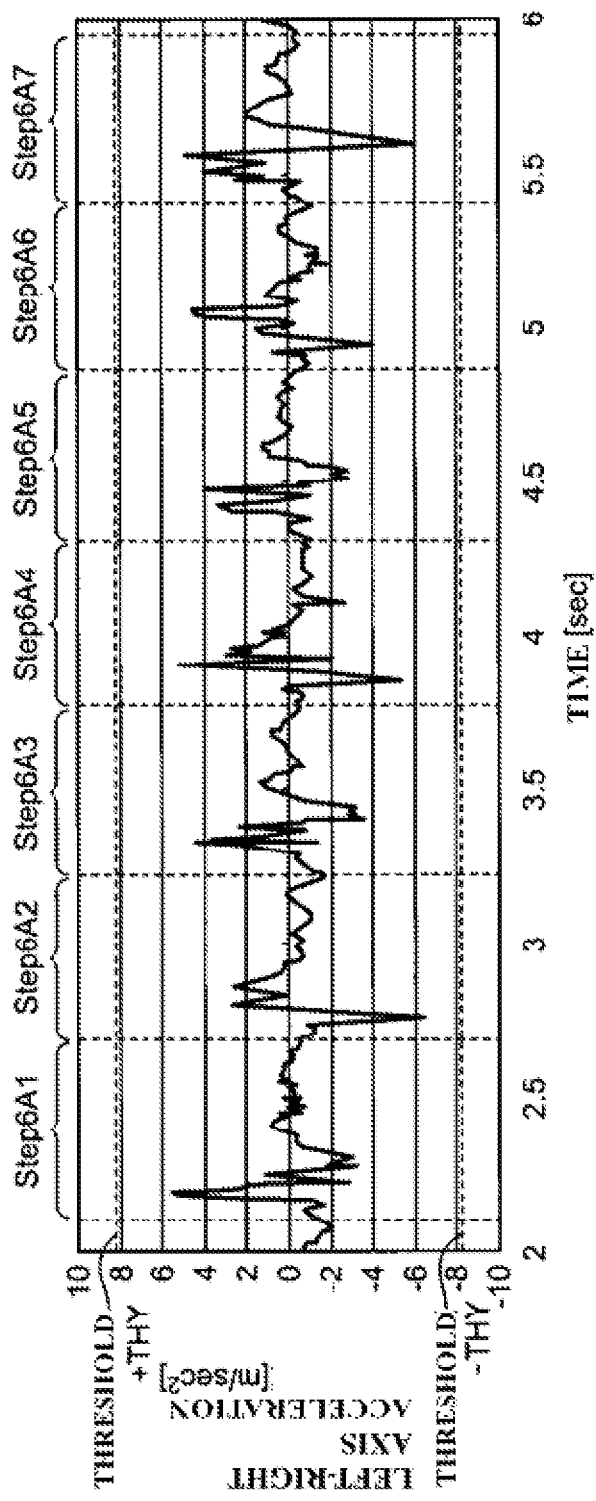
FIG. 6A is a graph illustrating an example of a left-right axis acceleration time change waveform obtained in the case where a person has walked in a linear manner.

FIG. 6A is a diagram illustrating an example of left-right axis acceleration time-series data obtained in the case where the measurement subject walks straight. Here, borders between each reference period are indicated by broken lines. As can be seen from FIG. 6A, in the case where the measurement subject walks straight, no extremely large values (for example, values whose absolute values exceed 8 m/s$^2$) appear in the left-right axis acceleration time-series data.

Figure 6B:
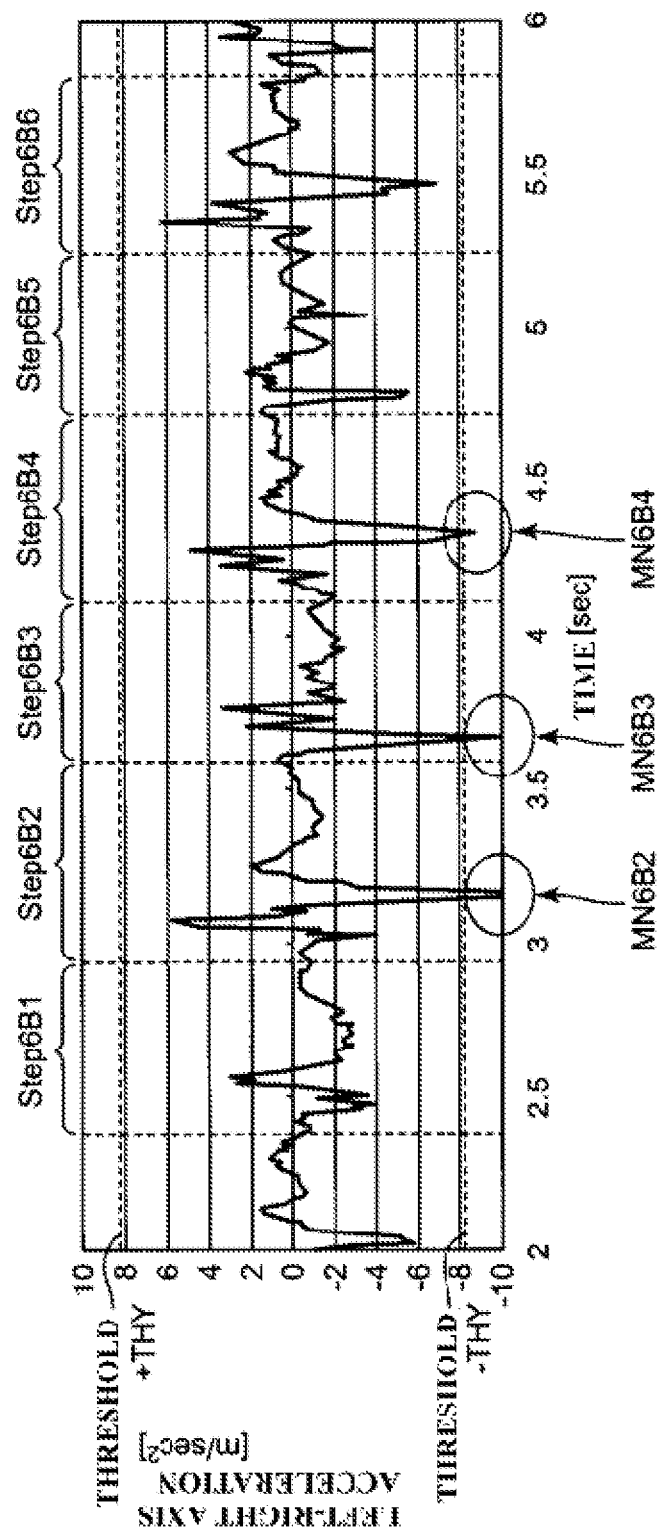
FIG. 6B is a graph illustrating an example of a left-right axis acceleration time change waveform obtained in the case where a person has walked in a non-linear manner (such as walking when turning a corner).

On the other hand, FIG. 6B is a diagram illustrating an example of the left-right axis acceleration time-series data obtained in the case where the measurement subject turns a corner or the like. As can be seen from FIG. 6B, when the measurement subject turns a corner or the like, extremely large values (for example, values whose absolute values exceed 8 m/s$^2$) appear in the left-right axis acceleration time-series data.

Accordingly, the error determination unit determines whether or not a predetermined threshold (for example, threshold+THY=+8 m/s$^2$, threshold−THY=−8 m/s$^2$) has been exceeded in the left-right axis acceleration time-series data obtained in that unit period (step S5). Then, in the case where it has been determined that the threshold has been exceeded in the left-right axis acceleration time-series data, the error determination unit determines that data for correctly evaluating the gait posture could not be obtained in that unit period and that a measurement condition error has therefore occurred ("NO" in step S6).

Figure 7A:
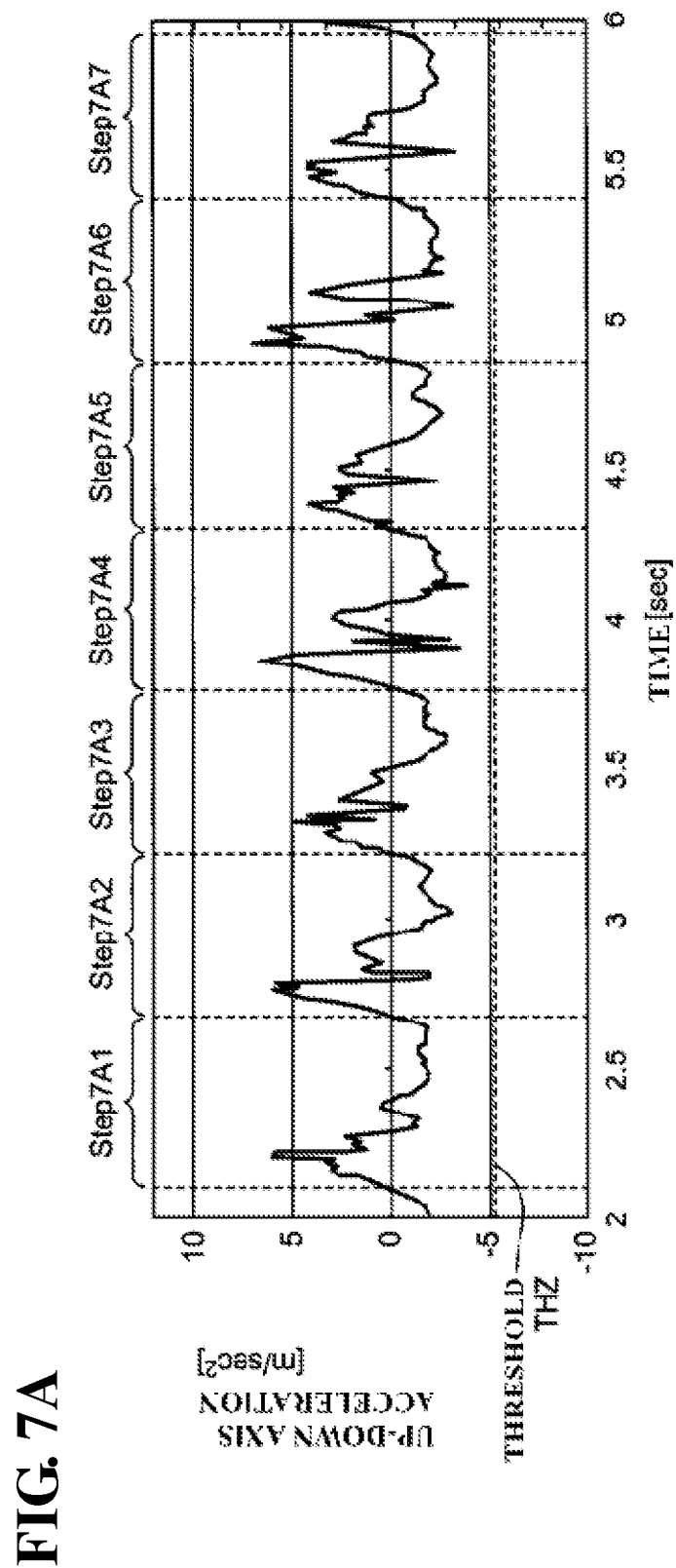
FIG. 7A is a graph illustrating an example of a left-right axis acceleration time change waveform obtained in the case where a person has walked in a manner suited to gait posture evaluation.

FIG. 7A is a diagram illustrating an example of up-down axis acceleration time-series data obtained in the case where the measurement subject walks without switching a hand that holds a bag. As can be seen from FIG. 7A, in the case where the measurement subject walks without switching a hand that holds a bag, no extremely low values (for example, values below −5 m/s$^2$) appear in the up-down axis acceleration time-series data.

Figure 7B:
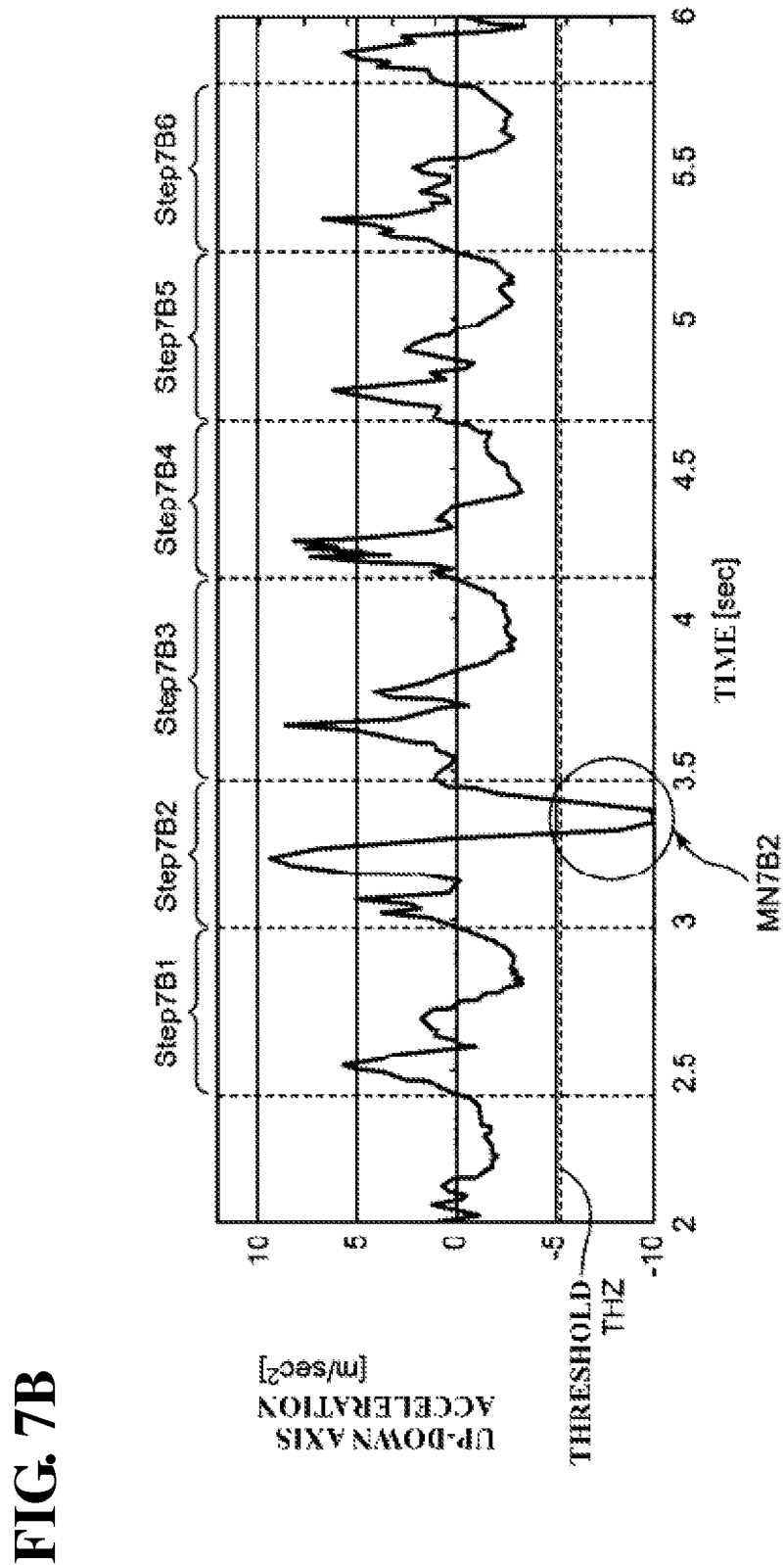
FIG. 7B is a graph illustrating an example of a left-right axis acceleration time change waveform obtained in the case where a person has walked while moving in a manner not suited to gait posture evaluation (a movement such as changing a hand that holds a bag).

On the other hand, FIG. 7B is a diagram illustrating an example of the up-down axis acceleration time-series data obtained in the case where the measurement subject has switched a hand that holds a bag while walking. As can be seen from FIG. 7B, in the case where the measurement subject has switched a hand that holds a bag while walking, an extremely small value (for example, a value below −5 m/s$^2$) appears in the up-down axis acceleration time-series data.

Accordingly, the error determination unit determines whether or not the up-down axis acceleration time-series data obtained in that unit period has dropped below a predetermined threshold (for example, threshold THZ=−5 m/s$^2$) (step S5). Then, in the case where it has been determined that the up-down axis acceleration time-series data has dropped below the predetermined threshold, the error determination unit determines that data for correctly evaluating the gait posture could not be obtained in that unit period and that a measurement condition error has therefore occurred ("NO" in step S6).

In this manner, the error determination unit determines whether or not the walker has taken a specific action (an action of turning a corner, an action of switching a hand that holds a bag, or the like) while walking that affects the evaluation of the gait posture in each unit period based on accelerations in one or more axes obtained in that unit period, and does not evaluate the gait posture, the left-right balance, and the like for that unit period in the case where it is determined that the measurement subject has taken such a specific action while walking. In addition, an evaluation amount for that unit period is not displayed in an evaluation result display, which will be mentioned later, and an indication of an measurement error is displayed instead. This makes it possible to avoid presenting an erroneous evaluation result to the user. In addition to the action of turning a corner and the action of switching a hand that holds a bag, the specific action may also include an action of avoiding an obstacle, a case where a predetermined number of steps (ten steps, for example) were not walked in the unit period due to the measurement subject waiting for a traffic signal, and so on. The error determination unit can determine whether or not such an action has been taken based on the output of the accelerometer 112 in such a case as well.

Next, the estimation of the gait posture (step S7) will be described. By operating as the evaluation unit, the control unit 110 calculates an amount (forward-shifted degree/rearward-shifted degree) corresponding to an imbalance (forward-shifted/rearward-shifted) in the front-rear direction of the position of the center of gravity of the measurement subject while walking, using the up-down axis acceleration time-series acceleration data in the unit period.

Figure 8A:
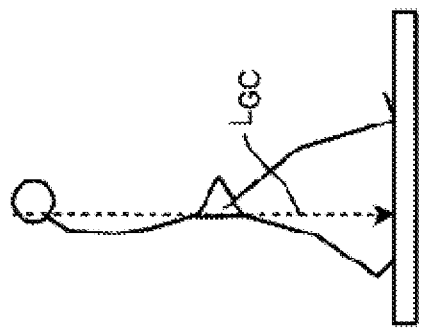
FIGS. 8A, 8B, and 8C are diagrams illustrating postures of a person while walking (timings at which the heel on a front leg makes contact with the ground).
Figure 8B:
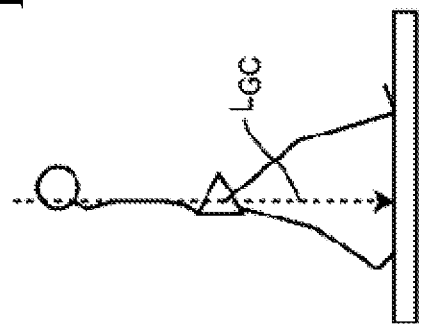
Figure 8C:
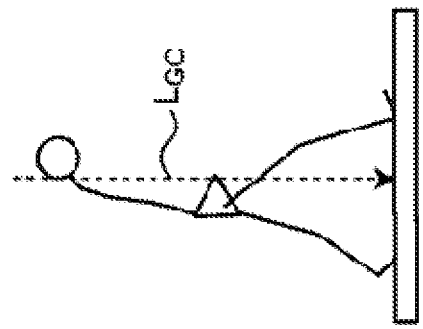

A method for estimating the gait posture (estimating the position of the center of gravity) will be described with reference to FIG. 8. FIGS. 8A, 8B, and 8C are diagrams illustrating postures of a person while walking (timings at which the heel on the front leg makes contact with the ground). FIG. 8A is a schematic diagram illustrating, from the side, a person whose center of gravity position during walking is in a forward-shifted position; FIG. 8B is a schematic diagram illustrating, from the side, a person whose center of gravity position during walking is near a center position; and FIG. 8C is a schematic diagram illustrating, from the side, a person whose center of gravity position during walking is in a rearward-shifted position.

Figure 8D:
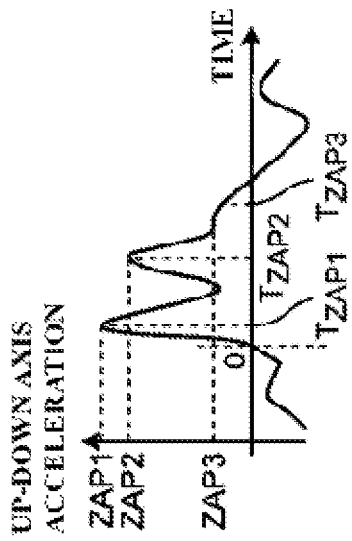
FIGS. 8D, 8E, and 8F are diagrams illustrating typical examples of up-down axis acceleration time change waveforms outputted by an accelerometer in a period spanning from the timing at which the heel on the front leg makes contact with the ground to the timing at which the rear leg, which is the lifted leg, matches the front leg, which is the loaded leg, in the travel direction.
Figure 8E:
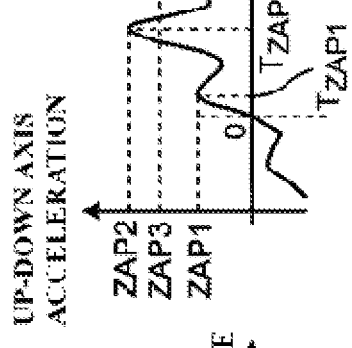
Figure 8F:
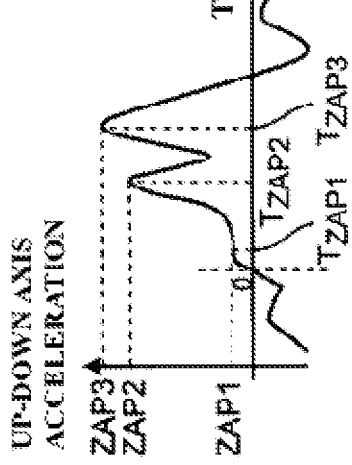

FIGS. 8D, 8E, and 8F are diagrams illustrating typical examples of up-down axis acceleration time change waveforms outputted by the accelerometer in a period spanning from the timing at which the heel on the front leg makes contact with the ground to the timing at which the rear leg, which is the lifted leg, matches the front leg, which is the loaded leg, in the travel direction. FIG. 8D is a typical example of an up-down axis acceleration time change waveform of a person whose center of gravity position is in a forward-shifted position (FIG. 8A); FIG. 8E is a typical example of an up-down axis acceleration time change waveform of a person whose center of gravity position is near a center position (FIG. 8B); and FIG. 8F is a typical example of an up-down axis acceleration time change waveform of a person whose center of gravity position is in a rearward-shifted position (FIG. 8C).

As can be seen by comparing FIGS. 8D, 8E, and 8F, compared to the up-down axis acceleration time change waveform of a person who walks with the center of gravity position in an area near a center area of the body (FIG. 8E), in the up-down axis acceleration time change waveform of a person who walks with a forward-shifted center of gravity position (FIG. 8D), a value ZAP1 of the maximum point that first appears in a single reference period (that takes a zero crossing point when the value switches from negative to positive) tends to decrease and a value ZAP3 of the maximum point that appears third tends to increase. These trends become more marked as the degree to which the center of gravity is shifted in the forward direction increases.

Conversely, compared to the up-down axis acceleration time change waveform of a person who walks with the center of gravity position in an area near a center area of the body (FIG. 8E), in the up-down axis acceleration time change waveform of a person who walks with a rearward-shifted center of gravity position (FIG. 8F), the value ZAP1 of the maximum point that first appears in a single reference period (that takes a zero crossing point when the value switches from negative to positive) tends to increase and the value ZAP3 of the maximum point that appears third tends to decrease. These trends become more marked as the degree to which the center of gravity is shifted in the rearward direction increases.

These trends can be summarized as follows.
(1) the greater a value obtained by dividing the value ZAP1 of a first maximum point by a value ZAP2 of a second maximum point in the same reference period (a forward-shifted degree Kg1 (Kg1=ZAP1/ZAP2)), the greater the degree that the position of the center of gravity of the person while walking (the forward-shifted degree) is shifted in the forward direction.
(2) the greater a value obtained by dividing the value ZAP3 of a third maximum point by the value ZAP2 of the second maximum point in the same reference period (a rearward-shifted degree Kg3 (Kg3=ZAP3/ZAP2)), the greater the degree that the position of the center of gravity of the person while walking (the rearward-shifted degree) is shifted in the rearward direction Note that dividing the value ZAP1 of the first maximum point and the value ZAP3 of the third maximum point by the value ZAP2 of the second maximum point in the same reference period when deriving the stated forward-shifted degree Kg1 and rearward-shifted degree Kg3 is a normalization for the purpose of reducing the influence of measurement environments, individual differences between measurement subjects, and so on.

The control unit 110 operating as the evaluation unit estimates the measurement subject's gait posture in the unit period by comparing the forward-shifted degree Kg1 and the rearward-shifted degree Kg3, for example, by finding a ratio between the forward-shifted degree Kg1 and the rearward-shifted degree Kg3. Ratios closer to 1 indicate that the center of gravity is in a position close to the center of the measurement subject with respect to the front-rear direction.

Next, estimation of the left-right balance (step S7) will be described. By operating as the evaluation unit, the control unit 110 calculates an amount corresponding to the measurement subject's left-right balance while walking (a difference between actions in a single step by the left foot and actions in a single step by the right foot) using acceleration time-series acceleration data in one or more axis directions in a unit period.

Figure 9:
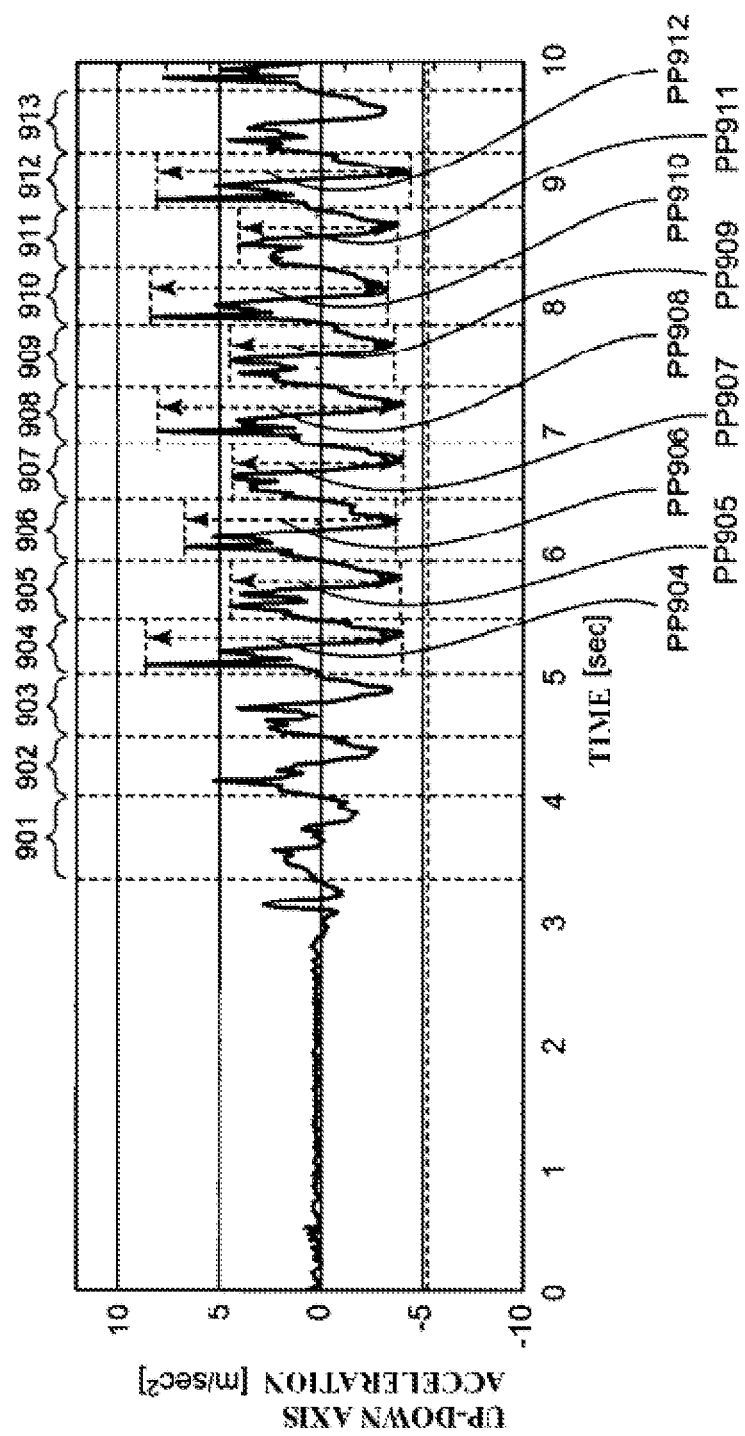
FIG. 9 is a graph illustrating a time change in an up-down axis acceleration outputted by an accelerometer.

FIG. 9 is a graph of up-down axis acceleration time-series data measured in a given unit period. By operating as the evaluation unit, the control unit 110 detects a maximum value and a minimum value of accelerations in each reference period (904, 905, 906, and so on), and finds PP values (PP904, PP905, PP906, and so on), which are differences between the maximum values and minimum values. Then, the evaluation unit finds a ratio between the PP values in even-numbered reference periods (the PP values in reference periods corresponding to a single step in which the left leg or the right leg is the supporting leg (PP904, PP906, and so on)) and the PP values in odd-numbered reference periods (the PP values in reference periods corresponding to a single step in which the right leg or the left leg is the supporting leg (PP905, PP907, and so on)). Ratios closer to 1 indicate that a difference in the walking actions (and in this case, swaying in the up-down direction in particular) is low in a reference period corresponding to one step in which the left leg and the right leg are supporting legs.

Likewise, the evaluation unit finds ratios between the PP values in even-numbered reference periods and the PP values in odd-numbered reference periods using the left-right axis acceleration time-series data and the front-rear axis acceleration time-series data, respectively. In this case as well, ratios closer to 1 indicate that a difference in the walking actions (and in this case, swaying in the left-right direction and swaying in the front-rear direction, respectively) is low in a reference period corresponding to one step in which the left leg and the right leg are supporting legs.

Figure 10:
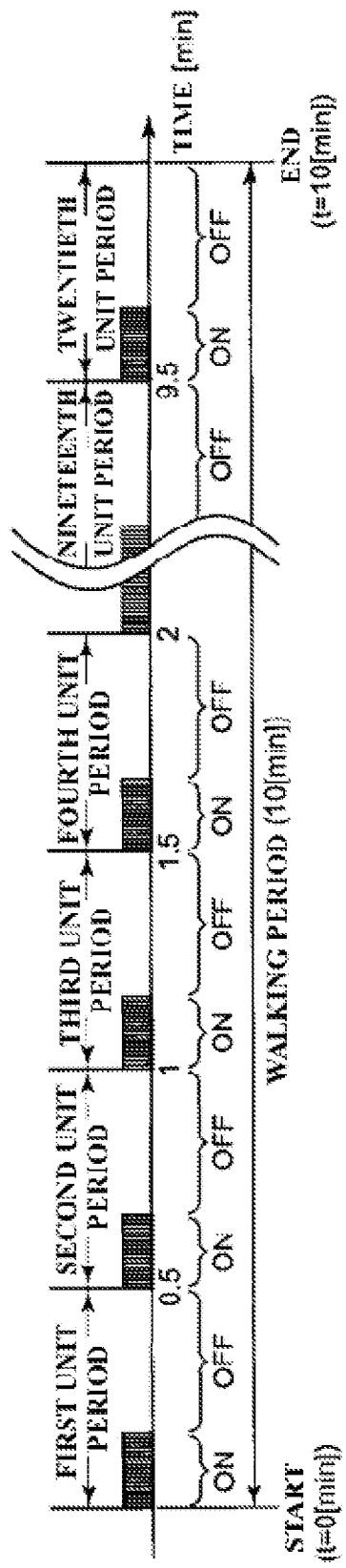
FIG. 10 is a schematic diagram illustrating a period in which the output of an accelerometer is obtained (a logging period) and a period in which the output of the accelerometer is not obtained (a non-logging period) in each of unit periods in a ten-minute walking period.

As described above, by operating as the evaluation unit, the control unit 110 obtains the outputs from the accelerometer 112 in only the first ten seconds of each unit period. After obtaining the outputs from the accelerometer 112 for ten seconds, the evaluation unit stops obtaining the outputs of the accelerometer. FIG. 10 is a timing chart illustrating the control unit turning the obtainment of the outputs from the accelerometer 112 on and off. In this manner, the control unit 110 obtains (logs) the acceleration data only for the first ten seconds (the logging period) in each unit period, and does not obtain the acceleration data in the remaining 20 seconds (the non-logging period). Even if the acceleration data is logged intermittently in this manner, the gait posture and left-right balance can be evaluated in the same manner as in the case where the acceleration data is continuously obtained throughout the entire walking period. Furthermore, the power consumed by the activity meter 100 can be greatly suppressed by logging the acceleration data intermittently in this manner.

Finally, by operating as the evaluation unit, the control unit 110 evaluates the gait posture and the left-right balance of walking actions in multiple stages each (step S9).

The evaluation unit evaluates the gait posture (imbalance in the center of gravity position) in each unit period in multiple stages by comparing, for example, the estimation result obtained in step S7 with a plurality of reference values. The evaluation unit gives a higher evaluation to the gait posture in that unit period the closer the center of gravity position is to the center (that is, the closer the ratio between Kg1 and Kg3 is to 1).

In addition, the evaluation unit evaluates the left-right balance in each unit period in multiple stages by comparing, for example, the estimation result obtained in step S8 with a plurality of reference values. The evaluation unit gives a higher evaluation to the left-right balance in that unit period the closer the ratio between the PP values in the even-numbered reference periods and the PP values in the odd-numbered reference periods is to 1. With respect to the up-down axis acceleration, the left-right axis acceleration, and the front-rear axis acceleration, it should be noted that in the case where the ratio between the PP values in the even-numbered reference periods and the PP values in the odd-numbered reference periods has been obtained, evaluations may be made independently for each of these accelerations, and three types of left-right balance evaluation amounts may be outputted for a single unit period.

In this manner, the evaluation unit outputs a single evaluation amount for the gait posture to the smartphone 200, and outputs one or more evaluation amounts for the left-right balance to the smartphone 200.

Figure 16:
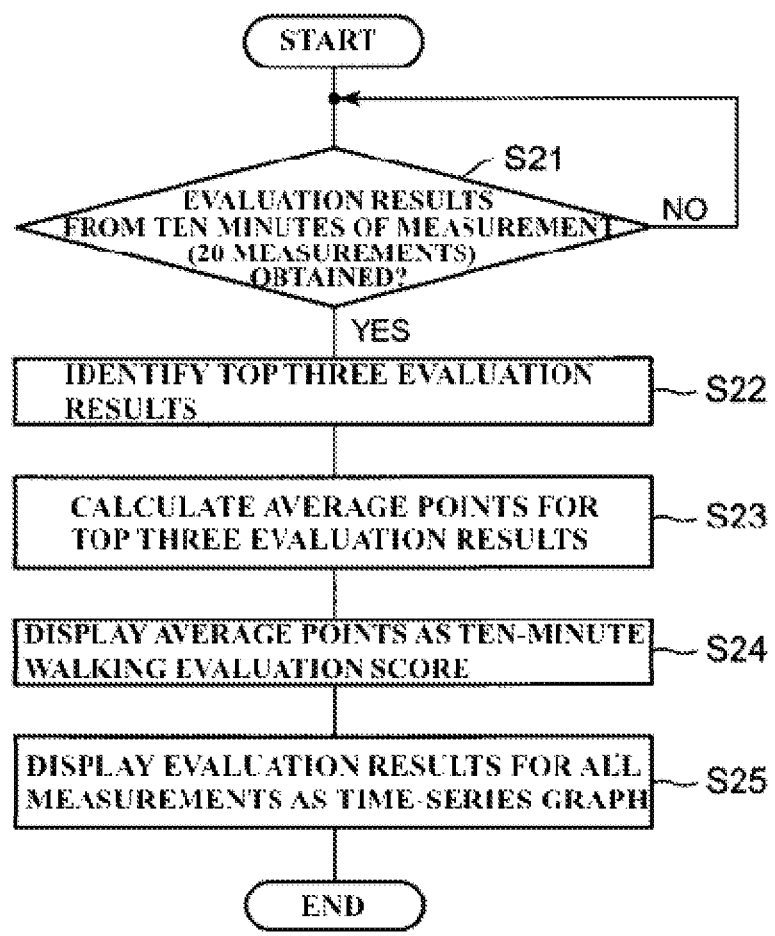
FIG. 16 is a diagram illustrating a flow of operations performed by a control unit of the smartphone that partially constitutes the gait posture meter.

Operations of the smartphone 200 will be described hereinafter. FIG. 16 is a diagram illustrating a flow of operations performed by the control unit 210 of the smartphone 200.

In step S21, the control unit 210 of the smartphone 200 checks whether or not the evaluation amounts for the gait posture and the left-right balance have been received from the activity meter 100 for the entire walking period. The evaluation amounts obtained by the control unit 210 are stored in the storage unit (the memory 220).

In step S22, by operating as the rank determination unit, the control unit 210 determines a rank for the plurality of evaluation amounts found repeatedly in each unit period, based on the dominance thereof.

In step S23, by operating as the score calculation unit, the control unit 210 derives a score by totaling the top three evaluation amounts according to the rank found by the rank determination unit. Note that the score calculation unit may derive an average of the top three evaluation amounts as the score. In addition, the evaluation amounts used to derive the score are not limited to the top three. The score calculation unit may derive the score using a predetermined number of the top evaluation amounts.

Figure 13:
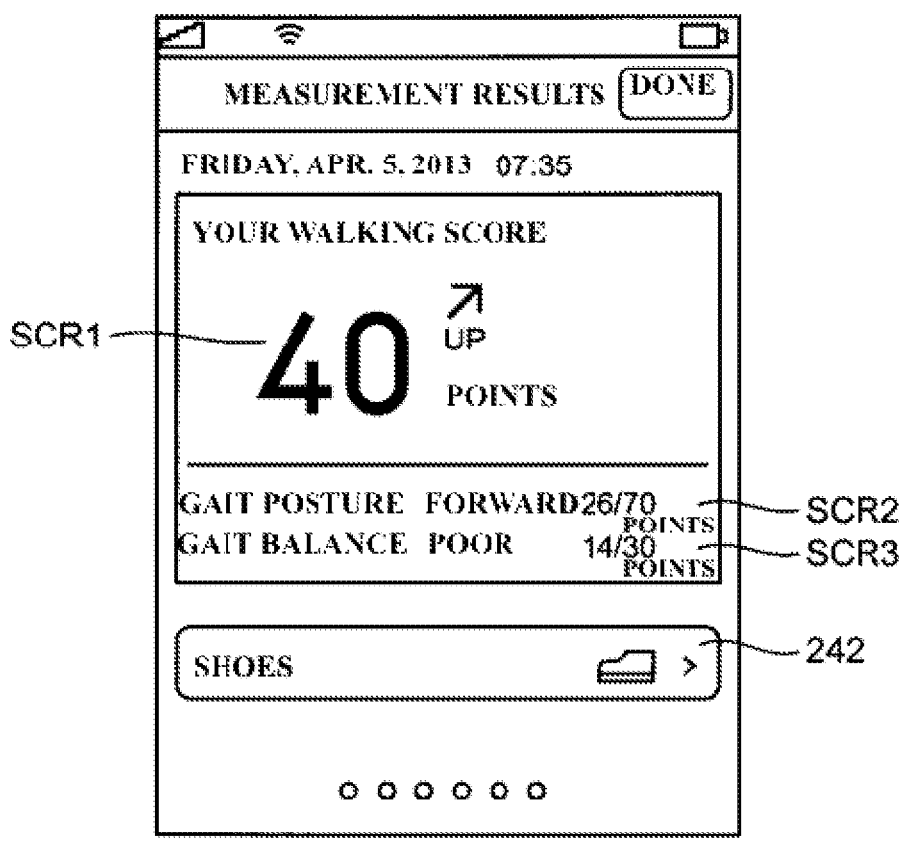
FIG. 13 is a diagram illustrating an example of a score display in a display screen (the display unit) of the stated smartphone.

In step S24, by operating as the score display processing unit, the control unit 210 displays the score (a ten-minute walking evaluation score) in the display screen (the display unit 240). FIG. 13 is an example of the score display. In this manner, a score SCR1 based on the top three evaluation amounts found in step S23 is displayed in the display screen (the display unit 240). By presenting the score based only on the top evaluation amounts to the user in this manner, the user can easily sense that his/her gait posture is improving as the gait posture measurement accumulate, which increases his/her desire to improve his/her gait posture. In addition to the score SCR1, comments and a score SCR2 regarding the gait posture, comments and a score SCR3 regarding the left-right balance (walking balance), and so on may be displayed in the display screen (the display unit 240) as well. In addition, as in the start instruction screen (FIG. 12), the button 242 may be provided for inputting data regarding the measurement subject's walking conditions.

Figure 14:
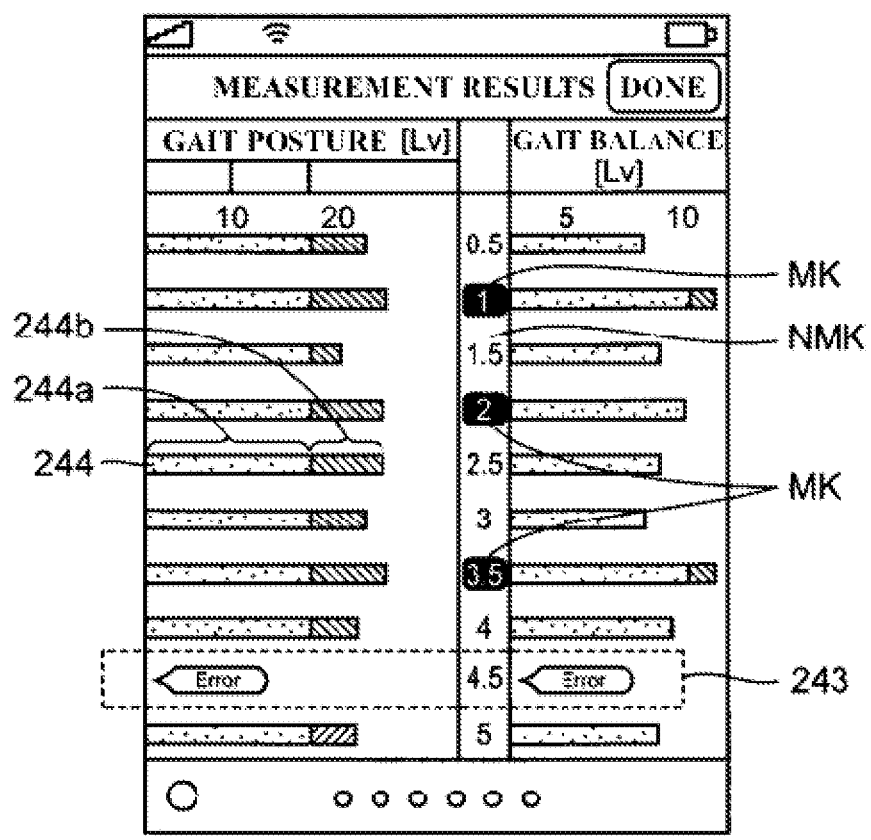
FIG. 14 is a diagram illustrating an example of a time-series display of evaluation amounts using a bar graph, in the display screen (the display unit) of the stated smartphone.

In step S25, by operating as the display processing unit, the control unit 210 arranges and displays, in time series, the evaluation amounts found in each unit period within the walking period (ten minutes), in the display screen (the display unit 240). FIG. 14 is a diagram illustrating an example in which the evaluation amounts repeatedly found in each unit period are displayed in the display screen (the display unit 240) as a bar graph. At this time, the display processing unit displays the top evaluation amounts in a manner that enables the user to visually distinguish the top evaluation amounts from the other evaluation amounts, in accordance with the rank determined by the rank determination unit in step S22. Here, displays MK for a unit period "1" (a unit period starting after one minute of the walking period has passed), a unit period "2" (a unit period starting, in the same manner, after two minutes of the walking period have passed), and a unit period "3.5" (a unit period starting after three minutes and 30 seconds of the walking period have passed) are displayed differently from displays NMK of the other unit periods, and thus the user can distinguish the time periods in which the top evaluation amounts were obtained.

In addition, using a predetermined reference value regarding the dominance of the evaluation amounts (here, Lv20 for the gait posture and Lv10 for the left-right balance (walking balance)), the display processing unit may display parts 244b of a bar graph 244 that corresponding to being greater than or equal to the reference value in an emphasized manner. This emphasized display may vary the display states of the parts 244b corresponding to being greater than or equal to the reference value and parts 244a corresponding to less than the reference value so that the user can visually distinguish between the two. Meanwhile, instead of the evaluation amounts, the display processing unit displays an error display 243 for an evaluation amount display in a unit period in which the control unit 110 (the error determination unit) of the activity meter 100 has determined that the acceleration time-series data was not measured correctly enough for the gait posture to be evaluated correctly.

Figure 15:
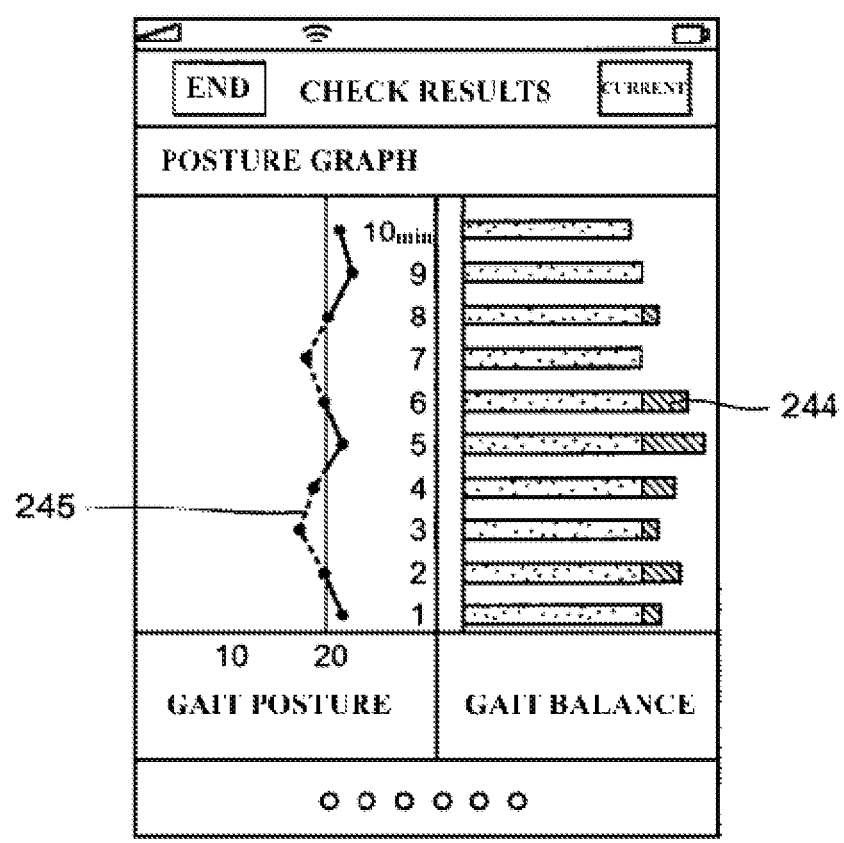
FIG. 15 is a diagram illustrating an example of a time-series display and a bar graph display of evaluation amounts using a polygonal line graph, in the display screen (the display unit) of the stated smartphone.

FIG. 15 is a diagram illustrating another example of an evaluation amount time-series display. As illustrated in FIG. 15, the evaluation amount time-series display may be made as a polygonal line graph. In this case, using a predetermined reference value regarding the dominance of the evaluation amounts (here, Lv20 for the gait posture), the polygonal line graph may display parts of the polygonal line graph 245 that correspond to being greater than or equal to the reference value in an emphasized manner. Using a bar graph, a polygonal line graph, or the like to display the evaluation amount time-series display in this manner is extremely useful in terms of facilitating understanding on the part of the user.

As described above, the gait posture meter according to the embodiment of the present invention can notify the user of transitions in the gait posture (positive and negative changes over time) in a period in which the user walks continuously in his/her normal everyday life, such as ten minutes at the most, for example. Accordingly, the user can easily know information such as whether or not s/he is continually walking correctly in his/her everyday periods of walking, at what timing his/her gait posture has worsened, and so on.

Figure 17:
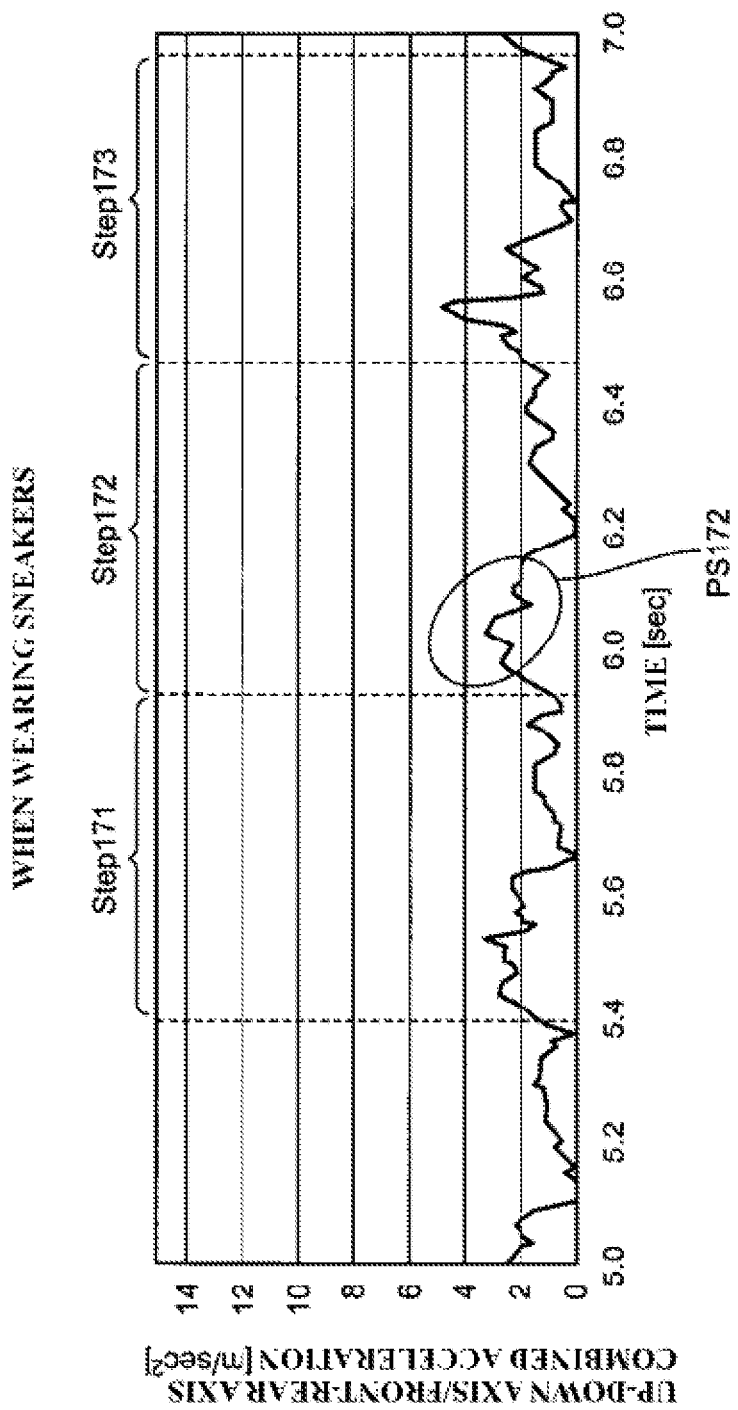
FIG. 17 is a graph illustrating an example of an up-down axis/front-rear axis combined acceleration time change waveform obtained when a measurement subject wears sneakers.
Figure 18:
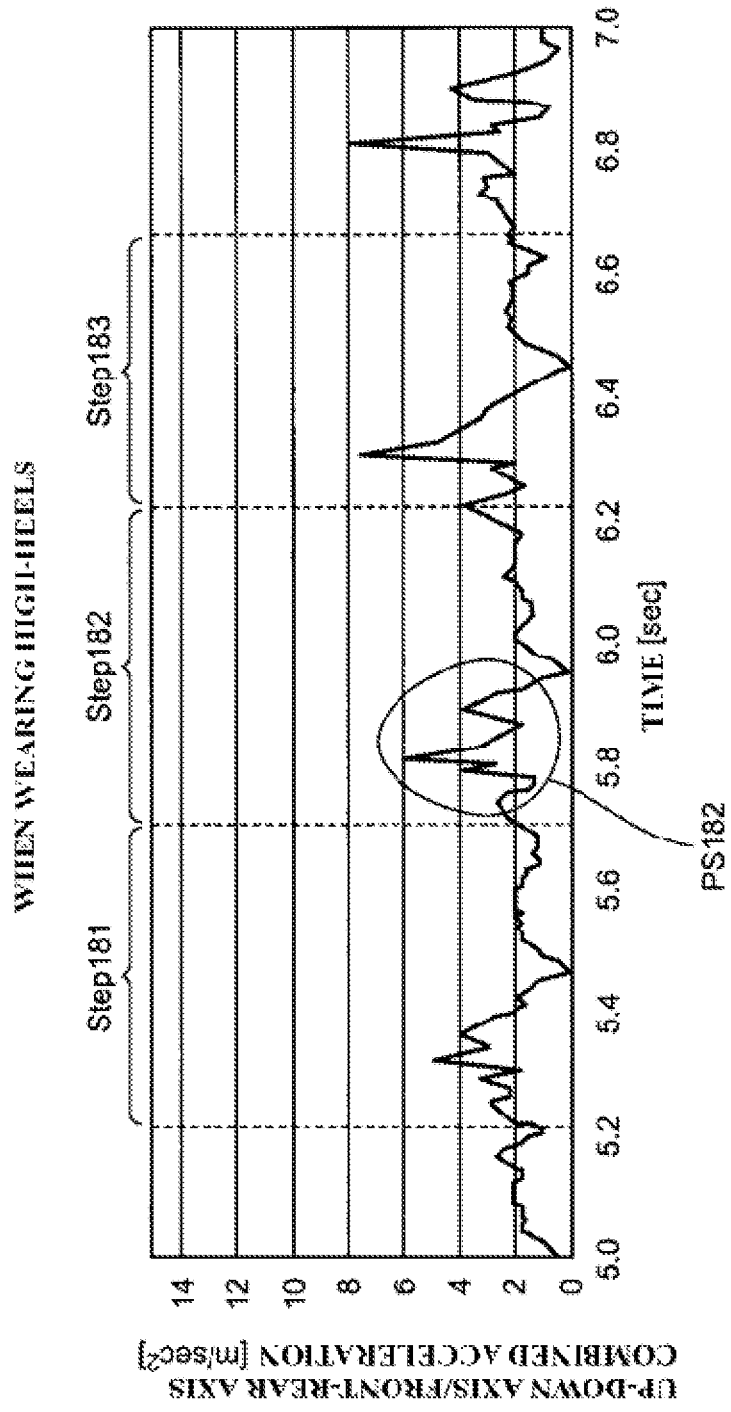
FIG. 18 is a graph illustrating an example of an up-down axis/front-rear axis combined acceleration time change waveform obtained when a measurement subject wears high-heels.

Finally, how differences in footwear used by the measurement subject for walking affect the measured accelerations, which in turn affects the gait posture evaluation results, will be described. Through research, the inventors of the present invention recognized that at least some measurement subjects walk differently due to different footwear. FIG. 17 is a waveform graph illustrating an up-down axis/front-rear axis combined acceleration obtained when the measurement subject walks while wearing sneakers. FIG. 18 is a waveform graph illustrating an up-down axis/front-rear axis combined acceleration obtained when the same measurement subject walks while wearing high-heels. In this manner, as can be seen from a waveform PS172 and a waveform PS182 in the former half of the reference period in the respective cases, the accelerations obtained for the same measurement subject tend to differ due to the effects of the footwear. Accordingly, taking differences in the measurement subject's walking conditions (for example, a condition of the type of footwear, in the present descriptions) into consideration is meaningful when evaluating the gait posture and the left-right balance. Accordingly, a configuration for the user to input the walking conditions (the type of footwear, for example) is added to the gait posture meter according to the embodiment of the present invention. The information of the walking conditions inputted by the user is stored in association with the evaluation amounts and used in later analyses.

Although the activity meter 100 and the smartphone 200 communicate with each other through BLE communication in the aforementioned embodiment, the invention is not limited thereto. For example, the activity meter 100 and the smartphone 200 may communicate through NFC (Near Field Communication) when the smartphone 200 and the activity meter 100 are near each other.

In addition, although the gait posture meter according to the present invention is described as being configured as a system including the activity meter 100 and the smartphone 200 in the aforementioned embodiment, the invention is not limited thereto.

For example, the gait posture meter according to the present invention may be constituted by the smartphone 200 only. Such a case assumes that the smartphone 200 includes an accelerometer. In addition, a program that causes the control unit 210 to quantitatively evaluate whether or not the gait posture of a person is a correct posture, and more specifically, a program that evaluates the positive and negative transition over time of the gait posture during everyday life, is installed in the memory 220 of the smartphone 200. Through this, the gait posture meter according to the present invention can be configured as a small-sized, compact unit.

This program can be recorded onto a recording medium such as a CD, a DVD, a flash memory, or the like as application software. By installing the application software recorded onto the recording medium in what is substantially a computer device, such as a smartphone, a personal computer, a PDA (personal digital assistant), or the like, that computer device can be caused to execute a method for quantitatively evaluating whether or not the gait posture of a person is a correct posture.

While preferred embodiments of the present invention have been described above, it is to be understood that variations and modifications will be apparent to those skilled in the art without departing from the scope and spirit of the present invention. The scope of the present invention, therefore, is to be determined solely by the following claims.

What is claimed is:

1. A gait posture meter that evaluates a gait posture of a measurement subject, the meter comprising:
    an accelerometer configured to be affixed to a centerline of a measurement subject's waist area so as to obtain acceleration data of the measurement subject while walking; and
    a processor configured or programmed to function as:
        a first timer that counts a predetermined continuous walking period which is no greater than ten minutes;
        a second timer that repeatedly counts a predetermined unit period, which is less than the predetermined continuous walking period, within the predetermined continuous walking period, the second timer also counts a logging period which is a predetermined and pre-set period of time within the predetermined unit period and a non-logging period which is a remaining period of time within the predetermined unit period, the logging period having a duration that is based only on the predetermined and pre-set period of time counted by the second timer;
        an evaluation unit that finds evaluation amounts quantitatively expressing a gait posture of the measurement subject based on the obtained acceleration data; wherein
    the processor controls whether or not to obtain outputs from the accelerometer such that, during the predetermined continuous walking period and within the predetermined unit period, the outputs from the accelerometer are obtained during the logging period and the outputs from the accelerometer are not obtained during the non-logging period such that the outputs from the accelerometer are obtained intermittently during the predetermined continuous walking period so as to suppress power consumption by the gait posture meter.

2. The gait posture meter according to claim 1, wherein the processor is configured or programmed to function as a display processing unit that controls a display screen to display the found evaluation amounts as a bar graph or a polygonal line graph.

3. The gait posture meter according to claim 2, wherein a reference value regarding a dominance of the evaluation amounts is set in advance; and
    in the bar graph or the polygonal line graph, the display processing unit controls the display screen to display a part of the bar graph or the polygonal line graph corresponding to a value greater than or equal to the reference value in an emphasized manner.

4. The gait posture meter according to claim 1, wherein the processor is configured or programmed to function as a rank determination unit that sets a rank of dominances among the found evaluation amounts;
    the processor is configured or programmed to function as a display processing unit; and
    of the found evaluation amounts, the display processing unit controls a display screen to display evaluation amounts in a highest predetermined number of rankings in a different manner than a manner in which other evaluation amounts are displayed.

5. The gait posture meter according to claim 4, wherein
the processor is configured or programmed to function as a score calculation unit that finds a score by totaling or averaging the evaluation amounts corresponding to the highest rankings; and
the processor is configured or programmed to function as a score display processing unit that controls the display screen to display the score found by the score calculation unit.

6. The gait posture meter according to claim 1, further comprising:
a memory that defines and functions as a storage unit that stores the found evaluation amounts,
wherein the storage unit stores data regarding walking conditions of the measurement subject in association with the found evaluation amounts.

7. The gait posture meter according to claim 6, wherein
the processor is configured or programmed to function as an information input unit that inputs information of footwear used when the measurement subject walks;
using the information input by the information input unit, the storage unit stores data regarding a type of footwear worn when the measurement subject walks as the data regarding the walking conditions; and
the processor is configured or programmed to function as a display processing unit that controls a display screen to display information indicating the type of the footwear.

8. The gait posture meter according to claim 1, wherein
the processor is configured or programmed to function as an error determination unit that determines whether or not to find the evaluation amount for each unit period based on the output of the accelerometer;
the processor is configured or programmed to function as a display processing unit; and
in the case where the error determination unit has determined that the evaluation amount cannot be found for a given unit period, the display processing unit controls a display screen to carry out an error display for that unit period instead of displaying the evaluation amount.

9. A non-transitory computer readable medium including a computer program for causing a computer to execute a method for evaluating a gait posture of a measurement subject, the method comprising:
obtaining an output of an accelerometer configured to be affixed to a centerline of the measurement subject's waist area so as to obtain acceleration data of the measurement subject while walking;
counting, using a processor, a predetermined continuous walking period which is no greater than ten minutes;
counting, using the processor, a predetermined unit period repeatedly within the predetermined continuous walking period, the predetermined unit period being less than the predetermined continuous walking period;
counting, using the processor, a logging period which is a predetermined and pre-set period of time within the predetermined unit period, the logging period having a duration that is based only on the predetermined and pre-set period of time counted by the processor;
counting, using the processor, a non-logging period which is a remaining period of time within the predetermined unit period;
finding, using the processor, evaluation amounts quantitatively expressing a gait posture of the measurement subject based on the obtained acceleration data; and
controlling, using the processor, whether or not to obtain outputs from the accelerometer such that, during the predetermined continuous walking period and within the predetermined unit period, the outputs from the accelerometer are obtained during the logging period and the outputs from the accelerometer are not obtained during the non-logging period such that the outputs from the accelerometer are obtained intermittently during the predetermined continuous walking period so as to suppress power consumption by a gait posture meter that includes the accelerometer and the processor.

* * * * *